US012607623B2

(12) United States Patent
Imoukhuede et al.

(10) Patent No.: US 12,607,623 B2
(45) Date of Patent: Apr. 21, 2026

(54) METHODS FOR EVALUATING ANGIOGENESIS

(71) Applicants: Princess Imoukhuede, St. Louis, MO (US); Yingye Fang, St. Louis, MO (US)

(72) Inventors: Princess Imoukhuede, St. Louis, MO (US); Yingye Fang, St. Louis, MO (US)

(73) Assignee: Washington University, St. Louis, MO (US)

( * ) Notice: Subject to any disclaimer, the term of this patent is extended or adjusted under 35 U.S.C. 154(b) by 295 days.

(21) Appl. No.: 17/107,023

(22) Filed: Nov. 30, 2020

(65) Prior Publication Data

US 2021/0208133 A1     Jul. 8, 2021

Related U.S. Application Data

(60) Provisional application No. 62/941,840, filed on Nov. 28, 2019.

(51) Int. Cl.
| | |
|---|---|
| *G01N 33/50* | (2006.01) |
| *G01N 33/543* | (2006.01) |
| *G01N 33/68* | (2006.01) |

(52) U.S. Cl.
CPC ... *G01N 33/5088* (2013.01); *G01N 33/54326* (2013.01); *G01N 33/6863* (2013.01); *G01N 2333/70596* (2013.01); *G01N 2333/71* (2013.01)

(58) Field of Classification Search
CPC ........... G01N 33/5088; G01N 33/6863; G01N 2333/70596; G01N 2333/71; G01N 33/5047; G01N 2800/044; G01N 2800/7014; G01N 33/54326
See application file for complete search history.

(56) References Cited

U.S. PATENT DOCUMENTS

| | | | |
|---|---|---|---|
| 8,557,531 B2 | 10/2013 | Lorence | |
| 2005/0064523 A1* | 3/2005 | Wu ..................... | G01N 33/5064 435/7.23 |

OTHER PUBLICATIONS

Weddell et al., (2014), Quantitative Characterization of Cellular Membrane-Receptor Heterogeneity through Statistical and Computational Modeling. PLoS ONE 9(5): e97271. doi:10.1371/journal.pone.0097271 (Year: 2014).*
Incio et al., Sci. Transl. Med. 10, eaag0945 (2018) (Year: 2018).*
Lazar et al. Transforming Growth Factor alpha: Mutation of Aspartic Acid 47 and Leucine 48 Results in Different Biological Activities . Mol. Cell. Biol., 8:1247-1252, 1988 (Year: 1988).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Brown et al., J Immunol. May 1996; 156(9):3285-91 (Year: 1996).*
Warzocha et al., Leukemia and Lymphoma (1997) vol. 24. pp. 267-281 (Year: 1997).*
Greenspan et al. 1999 Defining epitopes: It's not as easy as it seems; Nature Biotechnology, 17:936-937 (Year: 1999).*
Bork. Powers and Pitfalls in Sequence Analysis: The 70% Hurdle. Genome Research, 2000, 10:398-400 (Year: 2000).*
Skolnick et al., Trends Biotechnol. Jan. 2000; 18(1):34-9 (Year: 2000).*
Vajdos et al., J Mol Biol. Jul. 5, 2002;320(2):415-28 at 416 (Year: 2002).*
Aagaard et al., Advanced Drug Delivery Reviews 59 (2007) 75-86 (Year: 2007).*
Guido et al., Curr Med Chem. 2008; 15(1):37-46 (Year: 2008).*
McKeague et al., J Nucleic Acids. 2012;2012:748913. Epub Oct. 2, 20124 (Year: 2012).*
Marone G, Granata F (eds): Angiogenesis, Lymphangiogenesis and Clinical Implications. Chem Immunol Allergy. Basel, Karger, 2014, vol. 99, pp. 1-226 (Year: 2014).*
Clark et al., J. Med. Chem., 2014, 57 (12), pp. 5023-5038 (Year: 2014).*
Miosge, Proc Natl Acad Sci U S A. Sep. 15, 2015;112(37):E5189-98 (Year: 2015).*
Kulmanov et al., Bioinformatics, 34(4), 2018, 660-668 (Year: 2018).*
Arterbery, A.S., et al., "Hhex is necessary for the hepatic differentiation of mouse ES cells and acts via Vegf signaling," 2016, PLoS One 11(1): e0146806, 19 pages.
Asahara, T., et al., "Isolation of Putative Progenitor Endothelial Cells for Angiogenesis," 1997, Science, 275:964-967, 4 pages.
Baer, P.C., "Adipose-derived mesenchymal stromal/stem cells: An update on their phenotype in vivo and in vitro," 2014, World J Stem Cells, 6/3:256-265, 11 pages.
Baker, N. A., et al., "Differentiation and Metabolic Interrogation of Human Adipocytes," 2017, Methods Mol. Biol, 1566:61-76, 18 pages.
Bentley, K., et al., "Agent-based simulation of notch-mediated tip cell selection in angiogenic sprout initialisation," 2009, J Theor Biol, 250/1:25-41 pages.
Bertolini, F., et al., "The multifaceted circulating endothelial cell in cancer: towards marker and target identification," 2006, Nat Rev Cancer, 6:835-845, 11 pages.
Blann, A.D., et al., "Circulating Endothelial Cells, Biomarker of Vascular Disease," 2005, Thromb Haemost, 93:228-235, 8 pages.
Bordbar, A., et al., "Constraint-based models predict metabolic and associated cellular functions," 2014, Nat Rev Genetics 15:107-120, 14 pages.
Boumelhem, B.B., et al., "Flow cytometric single cell analysis reveals heterogeneity between adipose depots," 2017, Adipocyte 6/2:112-123, 13 pages.

(Continued)

*Primary Examiner* — Vanessa L. Ford
*Assistant Examiner* — Danaya L Middleton
(74) *Attorney, Agent, or Firm* — Stinson LLP

(57)     ABSTRACT

Various methods for isolating cell populations from adipocyte tissue and/or blood and quantifying levels of vascular endothelial growth factor receptors (VEGFR) on the isolated cell populations are provided. Also provided are methods of evaluating or modifying angiogenic therapy in a subject.

10 Claims, 25 Drawing Sheets

(56)                    References Cited

OTHER PUBLICATIONS

Breitling, R., "What is systems biology?" 2010, Front Physiol, vol. 1, Art. 9:1-5, 5 pages.

Cao Y., "Positive and negative modulation of angiogenesis by VEGFR1 ligands," 2009, Sci Signal, 22/59:1-12, 12 pages.

Cao, Y., "Angiogenesis and vascular functions in modulation of obesity, adipose metabolism, and insulin sensitivity," 2013, Cell Metab, 18:478-489, 12 pages.

Cao, Y., "Angiogenesis as a therapeutic target for obesity and metabolic diseases," 2014, Chem Immunol Allergy, 99:170-179, Abstrast Only.

Castiglione, F., et al., "Modeling biology spanning different scales: An open challenge," 2014, BioMed Research International, vol. 2014, Art. ID 902545, 9 pages.

Chen, S., et al., "Characterizing Glioblastoma Heterogeneity via Single-Cell Receptor Quantification," 2018, Front Bioeng Biotechnol, vol. 6, Art.92, 12 pages.

Chen, S., et al., "Chapter 8, qFlow cytometry-based receptoromic screening: a high-throughput quantification approach informing biomarker selection and nanosensor development," 2017, Methods Mol Biol, 2nd ed., S. Hurst Petrosko and E. S. Day, Eds. New York, NY: Springer New York, pp. 117-138.

Chen, S., et al., "Quantification of VEGFRs, NRP1, and PDGFRs on Endothelial Cells and Fibroblasts Reveals Serum, Intra-Family Ligand, and Cross-Family Ligand Regulation," 2015, Cell Mol Bioeng, 8/3:383-403, 21 pages.

Chopra, H., et al., "Insights into Endothelial Progenitor Cells: Origin, Classification, Potentials, and Prospects," 2018, Hindawi, vol. 2018, Article ID 9847015, 24 pages.

Chu, L.H., et al., "A multiscale computational model predicts distribution of anti-angiogenic isoform VEGF165b in peripheral arterial disease in human and mouse," 2016, Sci Rep, 6:73030, 11 pages.

Corvera, S., et al., "Adipose Tissue Angiogenesis: Impact on Obesity and Type-2 Diabetes," 2014, Biochimica et Biophysica Acta 1842:463-472, 10 pages.

Dada, J.O., et al., "Multi-scale modelling and simulation in systems biology," 2011, Integrative Biology 3:86-96, 11 pages.

Dalton, H.J., et al., "Macrophages facilitate resistance to anti-VEGF therapy by altered VEGFR expression," 2017, Clin Cancer Res, 23/22:7034-7046, 14 pages.

Danova, M., et al., "Flow cytometric analysis of circulating endothelial cells and endothelial progenitors for clinical purposes in oncology: A critical evaluation.," 2016, Mol Clin Oncol, 4/6:909-917, 9 pages.

Delorme, B., et al., "Presence of endothelial progenitor cells, distinct from mature endothelial cells, within human CD146+ blood cells," 2005, Thromb Haemost, 94:1270-1279, 10 pages.

Drake, T.A., "Genes and pathways contributing to obesity: a systems biology view," 2010, Prog Mol Biol Transl Sci, 94:9-38, 30 pages.

Duda, D.G., et al., "Differential CD146 Expression on Circulating Versus Tissue Endothelial Cells in Rectal Cancer Patients: Implications for CirculatingEndothelial and Progenitor Cells as Biomarkers for Antiangiogenic Therapy," 2006, J Clin Oncol, 24/9:1449-1453, 5 Pages.

Eidenschink, L., et al., "Basal levels of CD34 positive cells in peripheral blood differ between individuals and are stable for 18 months," 2012, Cytom Part B—Clin Cytom, 82B/1:18-25, 8 pages.

Elias, I., et al., "Adipose tissue overexpression of vascular endothelial growth factor protects against diet-induced obesity and insulin resistance," 2012, Diabetes, 61:1801-1813, 13 pages.

Emond, C., et al., "The Influence of Obesity on the Pharmacokinetics of Dioxin in Mice: An Assessment Using Classical and PBPK Modeling," 2018, Toxicol Sci 164(1):218-228, 11 pages.

Erban, R., et al., "A Practical Guide to Stochastic Simulations of Reaction-Diffusion Processes," Nov. 19, 2007, arXiv: 704.1908v2; https://doi.org/10.48550/arXiv0704.1908, 35 pages.

Estes, M.I., et al., "Identification of endothelial cells and progenitor cell subsets in human peripheral blood," 2010, Curr Protoc Cytom, Suppl. 52:9.33.1-9.33.11, 11 pages.

Figueredo, G.P., et al. "Comparing Stochastic Differential Equations and Agent-Based Modelling and Simulation for Early-Stage Cancer," 2014, PLoS One, 9/4:e95150; 18 pages.

Finley, S.D., et al., "Compartment Model Predicts VEGF Secretion and Investigates the Effects of VEGF Trap in Tumor-Bearing Mice,", 2013, Front Oncol, 3:Art 196, 22 pages, doi:10.3389/fonc.2013.00196.

Fukumura, D., et al., "Paracrine Regulation of Angiogenesis and Adipocyte Differentiation During In Vivo Adipogenesis," 2003, Circ Res, http://www.circresaha.org, 10 pages, doi:10.1161/01.res.0000099243.20096.fa. 93: e88-e97.

Gallagher, S., In Joint Statistical Meeting, Baltimore, 2017, "Comparing compartment and agent-based models," 21 pages.

Gao, J., et al., "Characterization of OP9 as authentic mesenchymal stem cell line," 2010, J Genet Genomics, 37:475-482, 8 pages.

Goldman, O., et al., "KDR identifies a conserved human and murine hepatic progenitor and instructs early liver development," 2013, Cell Stem Cell, 12:748-760, 13 pages.

Goon, P.K.Y., et al., "Detection and Quantification of Mature Circulating Endothelial Cells Using Flow Cytometry and Immunomagnetic Beads: A Methodological Comparison," 2006, Thromb Haemost, 96:45-52, 8 pages.

Grimstein, M., et al., "Physiologically Based Pharmacokinetic Modeling in Regulatory Science: An Update From the U.S. Food and Drug Administration's Office of Clinical Pharmacology," 2019, Journal of Pharmaceutical Sciences, 108:21-25, 5 pages.

Hanley, M.J., et al., "Effect of obesity on the pharmacokinetics of drugs in humans," 2010, Clin Pharmacokinet 49/2:71-87, 17 pages.

Hristov, M., et al., "Endothelial progenitor cells: Cellular Biomarkers in Vascular Disease," 2008, Drug Discovery Today: Disease Mechanisms, 5/3-4:e267-e271, Abstract only.

Huizer, K., et al., "Improving the characterization of endothelial progenitor cell subsets by an optimized FACS protocol," 2017, PLoS One, https://doi,org/10.1371/journal.pone.0184895, 18 pages. 12 (9) : e0184895.

Imoukhuede, P. I., et al., "Quantitative Fluorescent Profiling of VEGFRs Reveals Tumor Cell and Endothelial Cell Heterogeneity in Breast Cancer Xenografts," 2013, Cancer Med. 3/2:225-244, 20 pages.

Imoukhuede, P. I., et al., "Endothelial cell-by-cell profiling reveals the temporal dynamics of VEGFR1 and VEGFR2 membrane localization after murine hindlimb ischemia," 2013, Am J Physiol Heart Circ Physiol, 304:H1085-H1093, 9 pages, doi: 10.1152/ajpheart.00514.2012.

Imoukhuede, P. I., et al., "Expression of VEGF Receptors on Endothelial Cells in Mouse Skeletal Muscle," 2012, PLoS One 7/9:E44791, 11 pages, www.plosone.org.

Imoukhuede, P. I., et al., "Quantification and cell-to-cell variation of vascular endothelial growth factor receptors," 2011, Exp Cell Res, 317/955-965, 11 pages.

Incio, J., et al., "PlGF/VEGFR-1 signaling promotes macrophage polarization and accelerated tumor progression in obesity," 2016, Clin Cancer Res, 22(12):2993-3004, 13 pages, clincancerres.aacrjournals.org.

Jialal, I., et al., "Decreased Number and Impaired Functionality of Endothelial Progenitor Cells in Subjects with Metabolic Syndrome: Implications for Increased Cardiovascular Risk," 2010, Atherosclerosis, 211/1:297-302, 15 pages.

Jo, J., et al., "Hypertrophy and/or hyperplasia: Dynamics of adipose tissue growth, " 2009, PLoS Comput. Biol. 5/3: e1000324, 12 pages, www.ploscompbiol.org.

Karaman, S., et al., "Transgenic overexpression of VEGF-C induces weight gain and insulin resistance in mice," 2016, Sci Reports, 6:31566, 12 pages, doi:10.1038/srep31566, www.nature.com/scientificreports.

Khan, S.S., et al., "Detection of Circulating Endothelial Cells and Endothelial Progenitor Cells by Flow Cytometry," 2005, Cytometry Part B, Clinical Cytometry, 64B:1-8, 8 pages, doi:10.1002/cyto.b.2004, www.interscience.wiley.com.

(56) References Cited

OTHER PUBLICATIONS

Klar, A.S., et al., "Characterization of vasculogenic potential of human adipose-derived endothelial cells in a three-dimensional vascularized skin substitute," 2016, Pediatr Surg Int, 32:11 pages, doi 10.1007/s00383-015-3808-7.

Koch, S., et al., "Signal Transduction by Vascular Endothelial Growth Factor Receptors," 2011, Biochem J, 437:169-183, 15 pages.

Lemoine, A.Y., et al., "Adipose tissue angiogenesis in obesity," 2013, Thromb Haemost, 110:661-669, 8 pages.

Lewis, N.E., et al., "Constraining the metabolic genotype-phenotype relationship using a phylogeny of in silico methods," 2012, Nature Reviews Microbiology, 10(4):291-305, 27 pages.

Luo, Y., et al., "Macrophagic CD146 promotes foam cell formation and retention during atherosclerosis," 2017, Cell Res, 27:352-372, 21 pages.

Mamer, S.B., et al., "Discovery of High-Affinity PDGF-VEGFR Interactions: Redefining RTK Dynamics," 2017, Sci Rep, 7:16439, 14 pages.

Marçola, M., et al., "Endothelial Progenitor Cells in Tumor Angiogenesis: Another Brick in the Wall," 2015, Stem Cells, Int'l, vol. 2015, Art ID 832649, 10 pages, http://dx.doi.org/10.1155/2015/832649.

Martin-Padura, I., et al., "Circulating endothelial cells as biomarkers for angiogenesis in tumor progression," 2009, Front Biosci (Schol Ed), S1/3, pp. 304-318, 15 pages.

Masuda, N., et al., A Gillespie algorithm for non-Markovian stochastic processes: 2018, SIAM Review, 60/1:95-115, 21 pages.

Meier-Schellersheim, M., et al., "Multiscale modeling for biologists," 2009, WIREs System Biology and Medicine, Multiscale Modeling for Biologists, 1:4-14, 11 pages.

Meng, Q., et al., "Systems Biology Approaches and Applications in Obesity, Diabetes, and Cardiovascular Diseases," 2013, Current Cardiovascular Risk Reports, 7:73-83, 11 pages.

Mund, J.A., et al., "Flow cytometric identification and functional characterization of immature and mature circulating endothelial cells," 2012, Arterioscler Thromb Vasc Biol, 32/4:1045-1053, 9 pages.

Murakami, M., et al., "VEGFR1 tyrosine kinase signaling promotes lymphangiogenesis as well as angiogenesis indirectly via macrophage recruitment," 2008, Arterioscler Thromb Vasc Biol, 28:658-664, 7 pages.

Pavlopoulos, G.A., et al., "Using graph theory to analyze biological networks," 2011, BioData Mining, 4/10:1-27, 27 pages.

Peichev, M., et al., "Expression of VEGFR-2 and AC133 by circulating human CD34+ cells identifies a population of functional endothelial precursors," 2000, Blood, 95/3:952-958.

Pietrzyk, L., "Biomarkers Discovery for Colorectal Cancer: A Review on Tumor Endothelial Markers as Perspective Candidates," 2016, Disease Markers, vol. 2016, Art. ID 4912405, 11 pages.

Qu, Z., et al., "Multi-scale modeling in biology: How to bridge the gaps between scales?" 2011, Progress in Biophysics and Molecular Biology, 107:21-31, 11 pages.

Ross, M.D., et al., "Vasular Ageing and Exercise: Focus on Cellular Reparative Processes," 2016, Oxidative Medicine and Cellular Longevity, vol. 2016, Art. ID 3583956, 15 pages.

Sabatier, F., et al., "Circulating endothelial cells, microparticles and progenitors: key players towards the definition of vascular competence," 2009, J Cell Mol Med, 13/3:454-471, 18 pages.

Scheller, K., et al., "Circulating endothelial cells (CECs) and circulating endothelial progenitor cells (CEPCs) in selected diseases," 2014, Acta Angiol, 20/1:1-18, 18 pages.

Shaffer, R.G., et al., "Flow Cytometric Measurement of Circulating Endothelial Cells: The Effect of Age and Peripheral Arterial Disease on Baseline Levels of Mature and Progenitor Populations," 2006, Cytometry Part B, Clinical Cytometry, 70B:56-62, 7 pages.

Shantsila, E., MD, et al., "Endothelial Progenitor Cells in Cardiovascular Disorders," 2007, 49/7:741-752, 12 pages, J Am Coll Cardiol.

Sidney, L.E., et al., "Concise review: Evidence for CD34 as a common marker for diverse progenitors," 2014, Stem Cells, 32/6:1380-1389, 10 pages.

Silva, K.R., et al., "Stromal-vascular fraction content and adipose stem cell behavior are altered in morbid obese and bost bariatric surgery ex-obese women," 2015, Stem Cell Res & Ther, 6/72, 13 pages.

Simons, M., et al., "Mechanisms and regulation of endothelial VEGF receptor signalling," 2016, Nat Rev, Mol Cell Biol, 17:611-625, 15 pages.

Simons, M., "An inside view: VEGF receptor trafficking and signaling," 2012, Physiology, 27:213-222, 10 pages.

Smit, C., et al., "Obesity and drug pharmacology: a review of the influence of obesity on pharmacokinetic and pharmacodynamic parameters," 2018, Expert Opinion on Drug Metabolism and Toxicology, doi:10.1080/17425255.2018.1440287, 32 pages.

Stelling, J., "Mathematical models in microbial systems biology," 2004, Current Opinion in Microbiology, 7:513-518, 6 pages.

Steurer, M., et al., "Quantification of circulating endothelial and progenitor cells: comparison of quantitative PCR and four-channel flow cytometry," 2008, BMC Res. Notes, 1/71, 8 pages.

Tousoulis, D., et al., "Role of inflammation and oxidative stress in endothelial progenitor cell function and mobilization: Therapeutic Implications for Cardiovascular Diseases," 2008, Atherosclerosis 201, 236-247, 12 pages.

Tuzcu, Z.B., MD, et al., "Circulating endothelial cell number and markers of endothelial dysfunction in previously preeclamptic women," 2015, Am J Obstet and Gynec, 213/4:533.e1-533.e7, Abstract only.

Villaret, A., et al., "Adipose Tissue Endothelial Cells From Obese Human Subjects: Differences Among Depots in Angiogenic, Metabolic, and Inflammatory Gene Expression and Cellular Senescence," 2010, Diabetes 59:2755-2763, 9 pages.

Voros, G., et al., "Modulation of angiogenesis during adipose tissue development in murine models of obesity," 2005, Endocrinology 146/10:4545-4554, 10 pages.

Walpole, J., et al., "Multiscale Computational Models of Complex Biological Systems," 2013, Annu Rev Biomed Eng, 15:137-154, 18 pages.

Walpole, J., et al., "Agent-based model of angiogenesis simulates capillary sprout initiation in multicellular networks," 2012, Integrative Biol, Accepted Manuscript, doi: 10.1039/c5ib00024f, 15 pages.

Waltenberger, J., et al., "Different signal transduction properties of KDR and Flt1, two receptors for vascular endothelial growth factor," 1994, J Biol Chem, 269/43:26988-26995, 8 pages.

Wang, Q., et al., "Obstructive sleep apnea and endothelial progenitor cells," 2013, Patient Preference and Adherence, 2013/7:1077-1090, 14 pages.

Watt, S.M., et al., "Human endothelial stem/progenitor cells, angiogenic factors and vascular repair," 2010, J. R. Soc. Interface, 7:S731-S751, 22 pages.

Weddell, J.C., et al., "Computational Systems Biology for the VEGF Family in Angiogenesis," 2018, Encyclopedia of Cardiovascular Research and Medicine, Elsevier Inc., 659-676, 18 pages, doi: 10.1016/B978-0-12-809657-4.99548-6.

Weddell, J.C., et al., "Integrative meta-modeling identifies endocytic vesicles, late endosome and the nucleus as the cellular compartments primarily directing RTK signaling," 2017, Integr Biol, 9:464-484, 21 pages.

Weddell, J.C., et al., "VEGFR1 promotes cell migration and proliferation through PLCγ and PI3K pathways," 2017, npj Syst Biol and Appl, 4/1: 11 pages, doi:10.1038/s41540-017-0037-9.

Weddell, J.C., et al., "Quantitative characterization of cellular membrane-receptor heterogeneity through statistical and computational modeling," 2014, PLoS One, 9/5:e97271, 19 pages.

Weickhardt, A.J. et al., "Vascular endothelial growth factor D expression is a potential biomarker of bevacizumab benefit in colorectal cancer," 2015, British. J. Cancer, 113:37-45, 9 pages.

Winterbach, W., et al., "Topology of molecular interaction networks," 2013, BMC Syst. Biol., 7/90, 15 pages, http://www.biomedcentral.com/1752-0509/7/90.

Wolins, N.E., et al., "OP9 mouse stromal cells rapidly differentiate into adipocytes: characterization of a useful new model of adipogenesis," 2006, J Lipid Res, 47:450-460, 11 pages.

(56) References Cited

OTHER PUBLICATIONS

Wu, F.T.H., et al., "A systems biology perspective on sVEGFR1: its biological function, pathogenic role and therapeutic use," 2010, J Cell Mol Med, 14/3:528-552, 25 pages.

* cited by examiner

FIG. 14
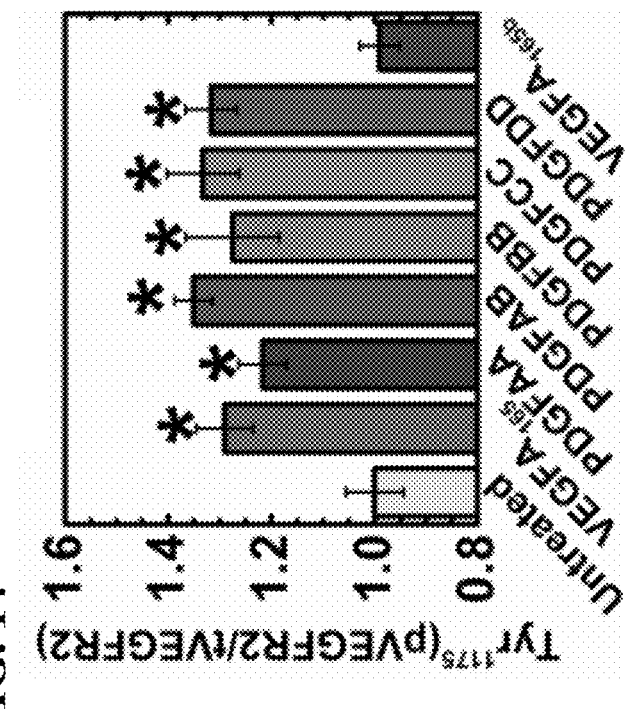
FIG. 12
FIG. 13
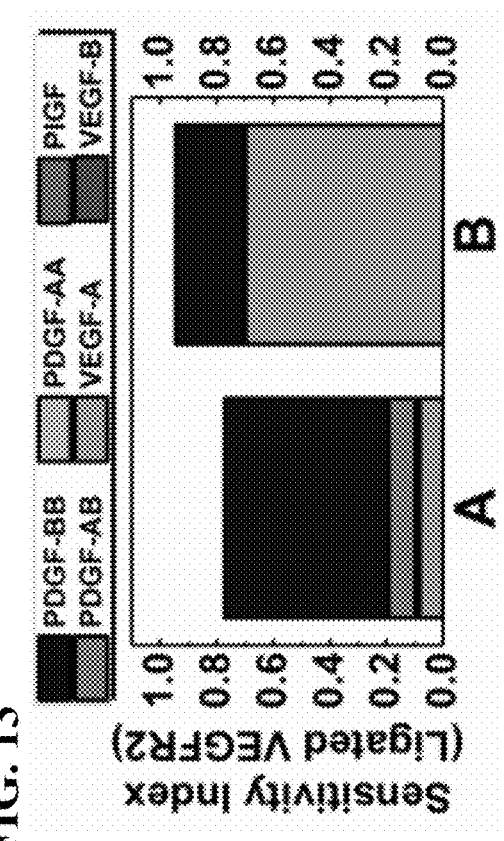

CD34+ Circulating Cell Enrichment Workflow

Table 1.

| Age*Sex Interactions (sample size) | VEGFR1 concentration on cEC | | VEGFR2 concentration on cEC | | VEGFR1 concentration on cPC | |
|---|---|---|---|---|---|---|
| | median | IQR | median | IQR | median | IQR |
| male, < 50 y/o (8)   male, ≥ 50 y/o (4) | NS | NS | NS | NS | NS | NS |
| female, < 50 y/o (5)   female, ≥ 50 y/o (6) | 0.001 | 0.0044 | 0.0187 | 0.0309 | 0.0035 | 0.0083 |
| female, < 50 y/o (5)   male, < 50 y/o (8) | 0.0054 | 0.0387 | NS (0.0532) | 0.0355 | NS | NS |
| female, < 50 y/o (5)   male, ≥ 50 y/o (4) | 0.0048 | NS (0.141) | NS | NS | NS | NS |
| female, ≥ 50 y/o (6)   male, ≥ 50 y/o (4) | NS (0.2264) | 0.0491 | NS | NS | 0.0251 | 0.0355 |

FIG. 22

Table 2.

| Subjects | Number of VEGFR1 per cPC | | Number of VEGFR1 per cEC | | Number of VEGFR2 per cEC | |
|---|---|---|---|---|---|---|
| | Median | IQR | Median | IQR | Median | IQR |
| Female | 2400 | 630 | 4500 | 4000 | 5300 | 10000 |
| postmenopausal, ≥ 50 y/o | 650 | 1500 | 2300 | 6000 | 2400 | 7400 |
| premenopausal, < 50 y/o | 88* | 214 | 25000 | 122000 | 18000 | 91000 |
| Male | 265 | 550 | 5000 | 52000 | 5400 | 50000 |
| ≥ 50 y/o | 250* | 390 | 4700 | 54000 | 5600 | 68000 |
| < 50 y/o | 330* | 2400 | 5200 | 13000 | 4300 | 9300 |

METHODS FOR EVALUATING ANGIOGENESIS

CROSS REFERENCE TO RELATED APPLICATIONS

This application claims the benefit to U.S. Provisional Application Ser. No. 62/941,840, filed Nov. 28, 2019, which is incorporated herein by reference in its entirety.

GOVERNMENT LICENSE RIGHTS

This invention was made with government support under 1653925 awarded by the National Science Foundation. The government has certain rights in the invention.

FIELD OF THE INVENTION

The present invention relates to methods for isolating cell populations from adipose tissue and/or blood and quantifying levels of vascular endothelial growth factor receptors (VEGFR) on the isolated cell populations. Also provided are methods of modifying angiogenic therapy in obese subjects as well as methods of characterizing VEGFR distributions in obese subjects.

BACKGROUND OF THE INVENTION

Angiogenesis fuels adipose tissue expansion, so targeting angiogenesis offers an attractive approach to treat obesity. Converging upon the ideal angiogenic targeting strategy is challenging: there is an angiogenic balance that correlates with healthy adiposity. However, pushing beyond that balance via either pro- or anti-angiogenic interventions can lead to worsened obesity-related comorbidities, like metabolic dysfunction. This suggests a need for more robust therapeutic approaches.

Highly vascularized adipose tissue is an obesity hallmark, so targeting adipose vasculature is a promising therapeutic approach. However, vascular targeting has yielded conflicting outcomes in pre-clinical models, suggesting a need to understand better adipose stromal-vascular fractions (SVFs). Vascular endothelial growth factor receptors (VEG-FRs) are key mediators of angiogenesis, and their abundance on vascularized tissues can negate the efficacy of angiogenic therapies. Despite this regulatory role, VEGFR distributions on adipocytes and SVFs are not fully characterized. There is a need for measuring VEGFRs on a cell-by-cell basis on obese individuals with lipedema; these patients presented disproportionally higher fat accumulation in the lower body than upper body. These methods can improve obesity therapeutics, which would benefit over 650 million obese patients worldwide.

Accordingly, there is a need for isolating specific cell populations, both from stromal vascular fractions and from blood. There is also a need for an effective method of quantifying surface VEGF receptors expressed on these cell types.

BRIEF SUMMARY OF THE INVENTION

Various aspects of the present invention are directed to methods of isolating cell populations in a stromal vascular fraction using flow cytometry and quantifying levels of vascular endothelial growth factor receptor (VEGFR) on the surface of individual cells in the isolated cell populations.

Further aspects of the present invention are directed to methods of evaluating angiogenesis in a subject having or at risk of developing obesity. The methods comprise (a) isolating a stromal vascular fraction (SVF) in an adipocyte (e.g., derived from visceral or subcutaneous adipose) tissue sample obtained from the subject; (b) isolating a subpopulation of cells from the SVF using flow cytometry; (c) quantifying VEGFR expression on the cell subpopulation; and (d) determining an amount of angiogenesis occurring in the subject based on the levels of VEGFR expression on the surface of the cell subpopulation.

Still further aspects of the present invention are directed to methods of determining the suitability of an anti-angiogenesis treatment in an obese subject. The methods comprise (a) isolating stromal vascular fraction (SVF) from an adipocyte (e.g., derived from subcutaneous adipose) tissue sample obtained from subject; (b) isolating a subpopulation of cells from the SVF using flow cytometry; (c) quantifying levels of VEGF receptors on cells; and (d) identifying the subject as a candidate for anti-angiogenesis treatment if the levels of VEGFR on the isolated subpopulation of cells exceed a threshold.

Another aspect of the present invention is directed to methods of isolating different cell populations from a blood sample. The methods can comprise (a) isolating CD34+ cells from the blood sample; (b) labeling the CD34+ cells with cell markers against CD31 and CD146; (c) isolating $CD34^+$ $CD31^+CD146^-$ as blood progenitor cells (e.g., bone marrow-derived hematopoietic progenitor cells); (d) isolating $CD34^+CD31^+CD146^+$ as mature endothelial cells; and (e) isolating $CD34^+CD31^+CD146^{dim}$ as endothelial progenitor cells.

Another aspect of the present invention is directed to methods of isolating different cell populations from a blood sample. The methods can comprise (a) isolating CD34+ cells from the blood sample; (b) labeling the CD34+ cells with cell markers against CD31 and CD146; (c) isolating $CD34^+$ $CD31^+CD146^-$ as blood progenitor cells (e.g., bone marrow-derived hematopoietic progenitor cells); and (d) isolating $CD34^+CD31^+CD146^+$ as circulating endothelial cells (such has those shed from blood vessels).

Other objects and features will be in part apparent and in part pointed out hereinafter.

BRIEF DESCRIPTION OF THE FIGURES

FIG. 10 also shows upper body (panels C-E) and lower body (panels F-H) cell-by-cell analysis of VEGFR1 (panels C and F), VEGFR2 (panels D and G), and VEGFR3 (panels E and H)) on stromal vascular fraction cells in obese (lipedema) patients.

FIG. 12 shows the affinity of various PDGFR ligands for the VEGFR receptor.

FIG. 13 depicts two different models wherein model A represents high plasma membrane concentrations of VEGFR and model B represents slow receptor endocytosis.

FIG. 14 shows levels of VEGR phosphorylation. 8 min of 10 mg/ml ligand phosphorylated VEGFR2 on HUVECs vs. untreated (n=8) based on power analysis and significance (*<0.05) and relative to untreated cells, via two-tailed Student's t-test.

CD34+CD31+ cells are non-endothelial hematopoietic progenitor cells (HPCs) and possibly cEPCs because some conflicting reports found that cEPCs are CD146–.

Figure 16A:
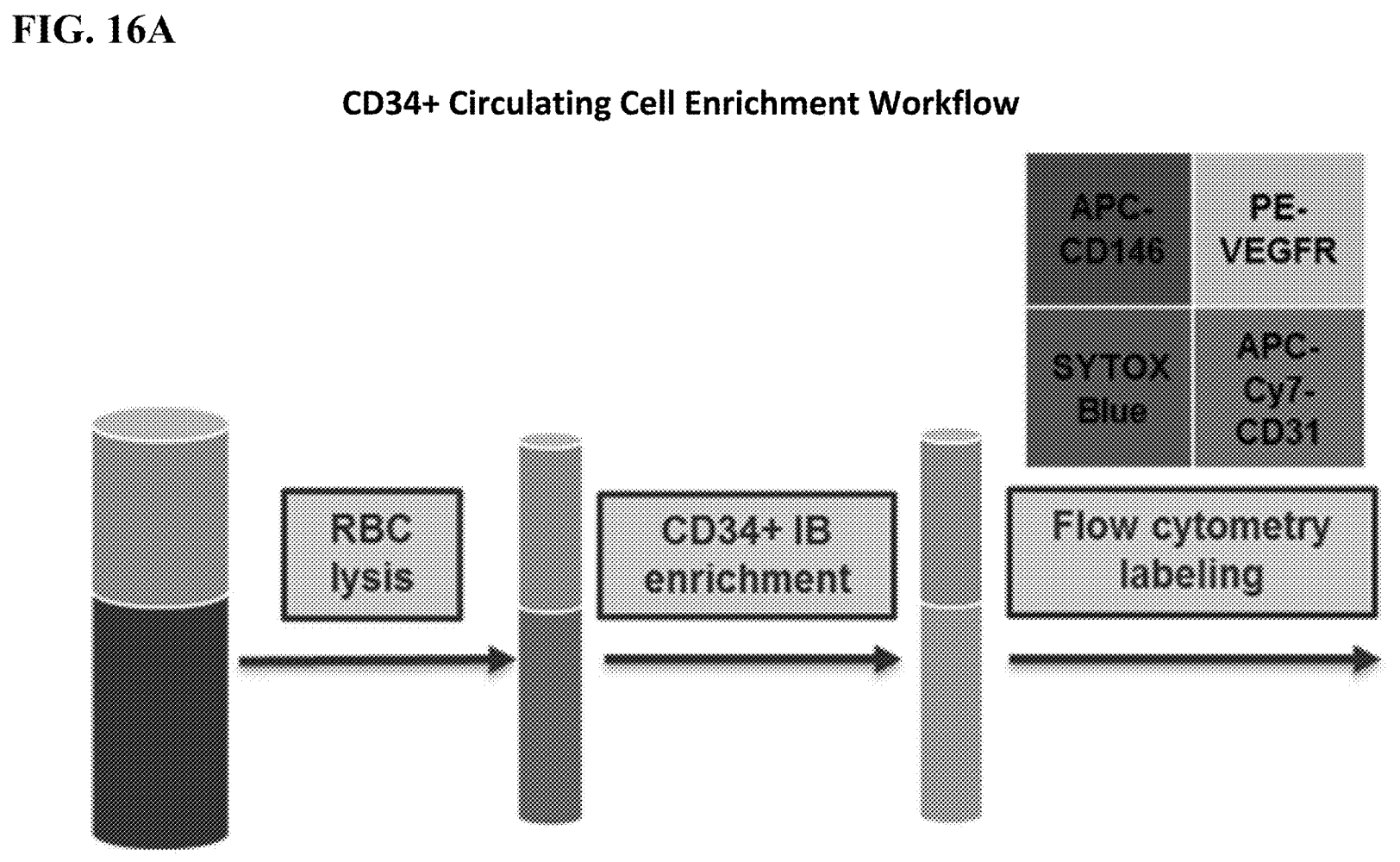
Figure 16B:
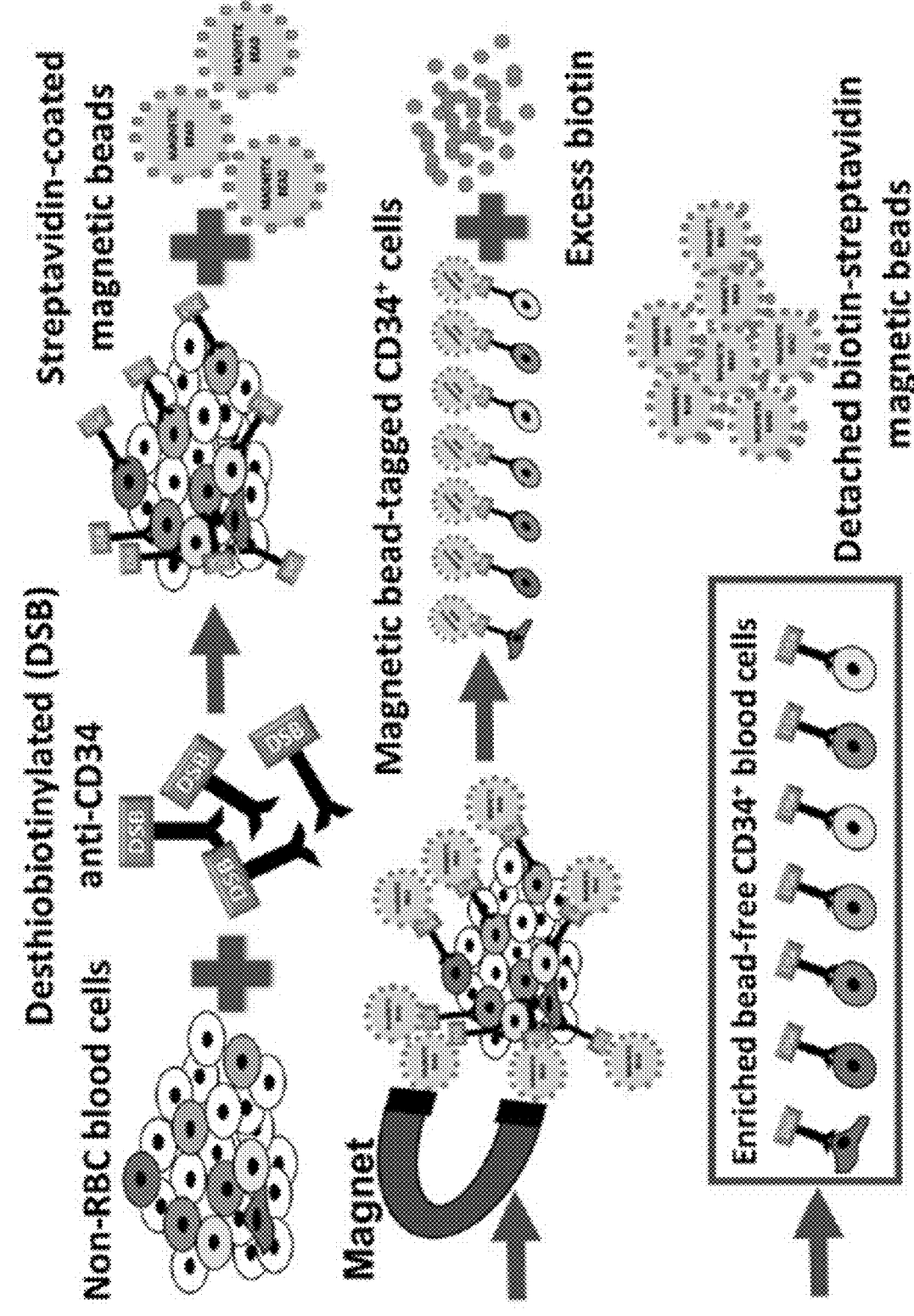

FIG. 16A shows the overview of an efficient workflow for CD34+ circulating cell enrichment and multicolor immunostaining for flow cytometric analysis. Flow-compatible CD34+ circulating cells were gently isolated from RBC-free peripheral blood via steps diagramed in FIG. 16B (~3 hours). Bead-free CD34+ circulating cells were labeled with 3 fluorochrome-conjugated antibodies and a viability dye.

FIG. 16B depicts a method of isolating CD34+ cells using magnetic beads.

Figure 17:
Figure 17:
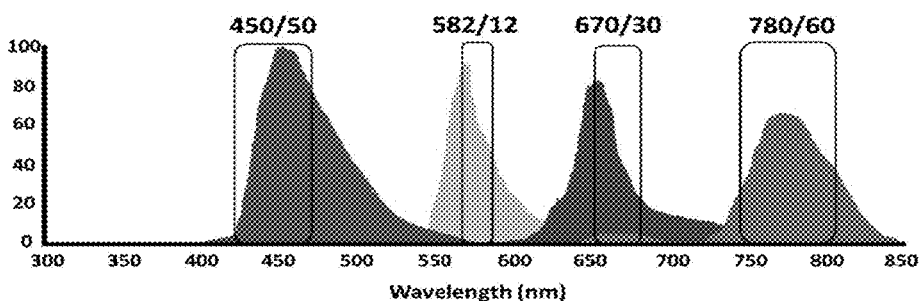
Figure 17:
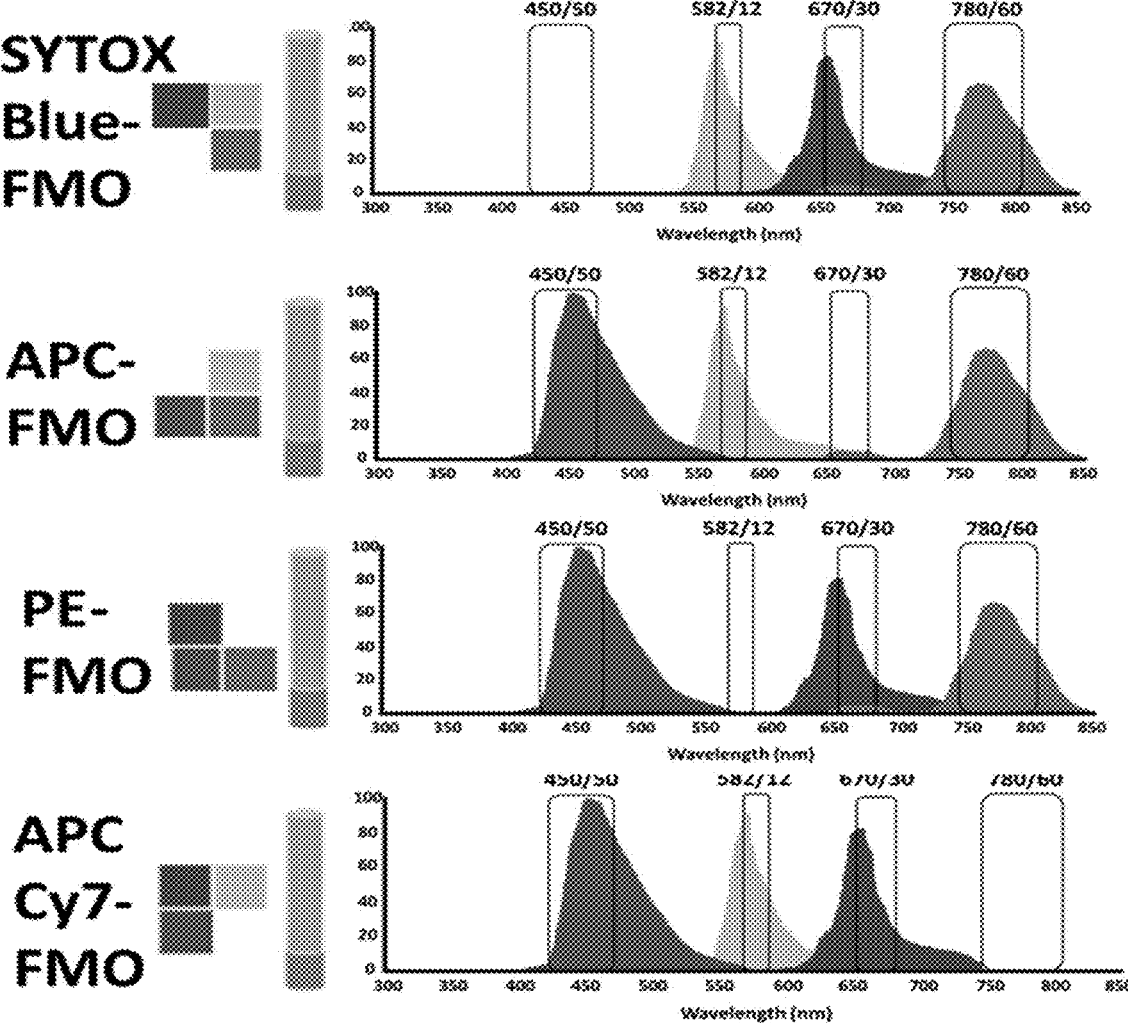

FIG. 17 visually depicts the multiple fluorescent channels used in the flow cytometry analysis. The plot on the left shows minimum overlap between the emission spectra and the ranges of band filters (BD Fortessa™ II). Graphs on the right show how fluorescence-minus-one (FMO) controls were used to determine positive/negative gates. Fluorescence signals detected in the FMO channels are spillover noises.

Figure 18:
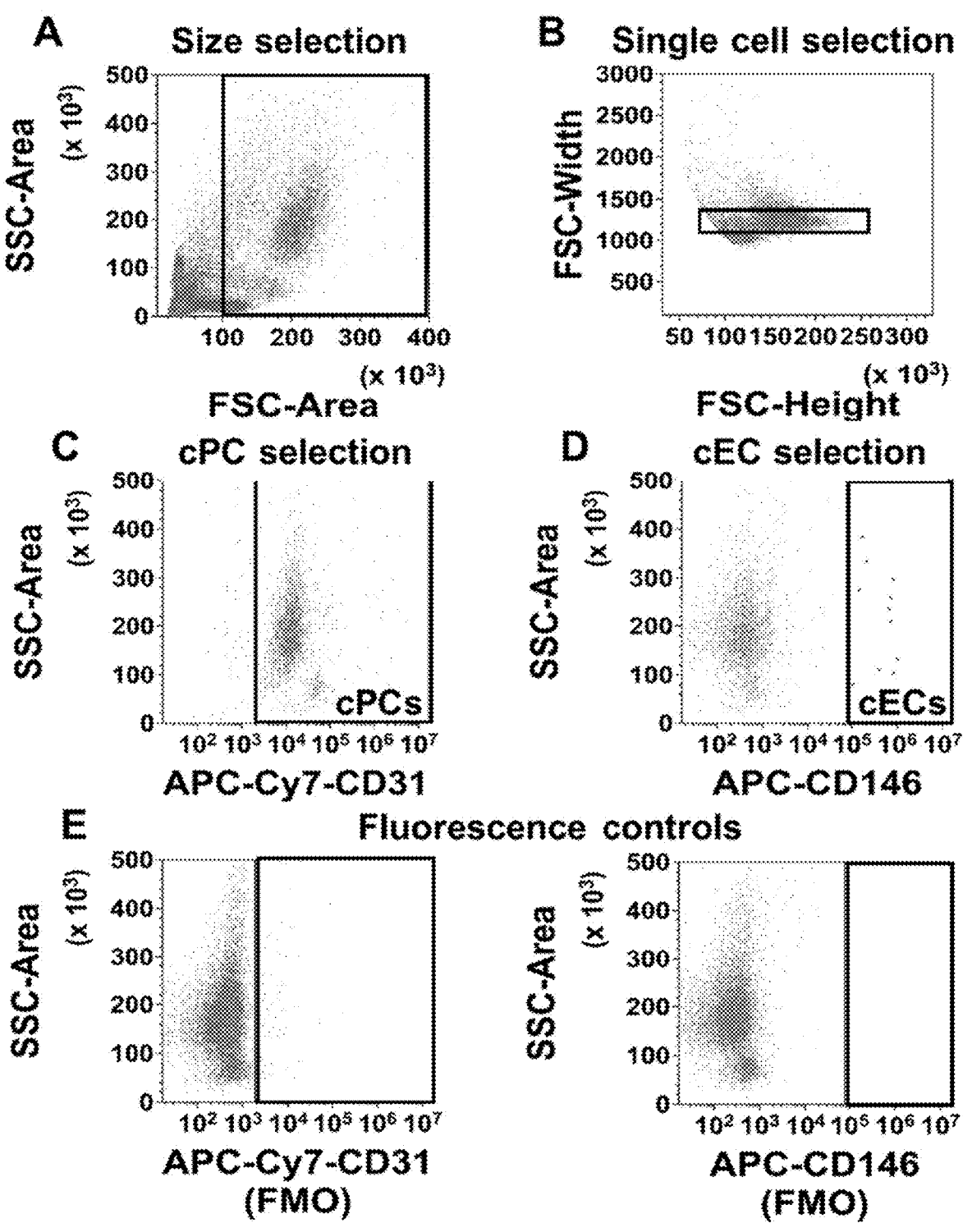

FIG. 18 depicts the flow cytometric gating schematic. Circulating progenitor cells (cPCs) and circulating endothelial cells (cECs) were identified in the pre-enriched CD34$^+$ cell population. (A) Debris and small platelets (≤6 μm) were excluded from the pre-enriched CD34+ cells. (B) Cell singlets were selected based on cell width (FSC-Width). (C) cPCs were identified as CD34$^+$ CD31$^+$ cells. (D) cECs were identified as CD34$^+$ CD31$^+$ CD146$^+$ and were rare in the healthy blood samples, comprising 0.98±0.29% of the cPC population (n=23, mean±SEM). (E) Fluorescence controls (i.e., FMO) of APC-Cy7-CD31 and APC-CD146 were used to set the respective positive gates.

Figure 19:
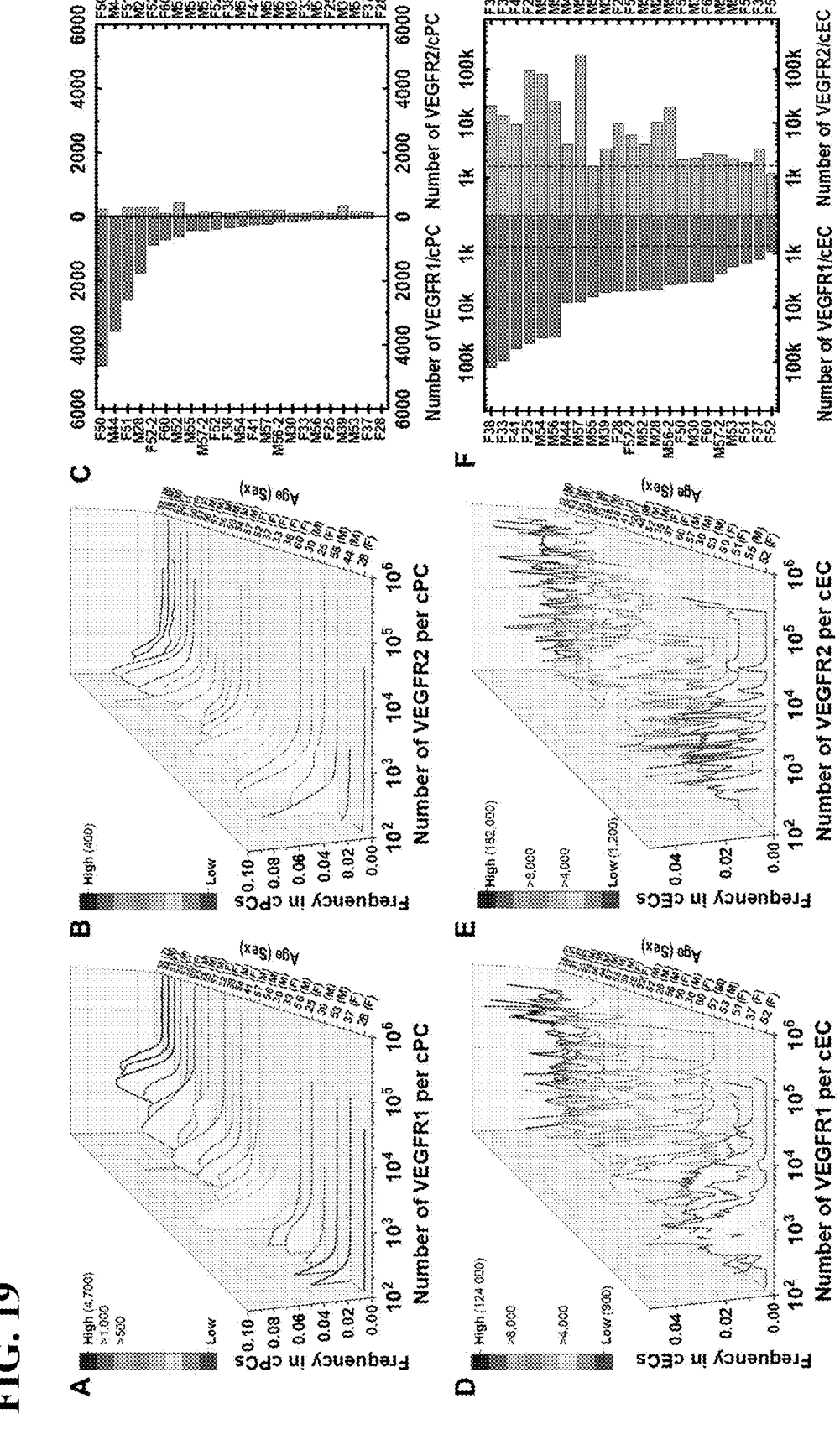

FIG. 19 shows cell-by-cell variations of VEGFR expression by CD34$^+$CD31$^+$ cPCs and CD34$^+$CD31$^+$CD146$^+$ cECs in 23 healthy blood samples. The distribution curves are ranked by median VEGFR concentrations from low to high (greyscale maps). (A) Cell-by-cell distributions of VEGFR1 and (B) VEGFR2 on cPCs in 23 individuals' blood (age 46±11, 11 females and 12 age-matched males). (C) Median levels of VEGFR1 and VEGFR2 on cPCs were extracted from the cell-by-cell distribution curves. (D) Cell-by-cell distributions of VEGFR1 and (E) VEGFR2 on cECs in 23 individuals' blood. (F) Median levels of VEGFR1 and VEGFR2 on cECs were extracted from the cell-by-cell distribution curves. Dashed lines indicate the previously reported ensemble averages of VEGFR1 and VEGFR2 concentrations of in-vitro human endothelial cells.

FIG. 20/Table 1 shows significant effects of age*sex interactions on VEGFR concentrations of cECs and cPCs. Median and IQR values of VEGFR distributions were compared across 23 healthy samples. NS=non significant (p>0.05).

Figure 21:
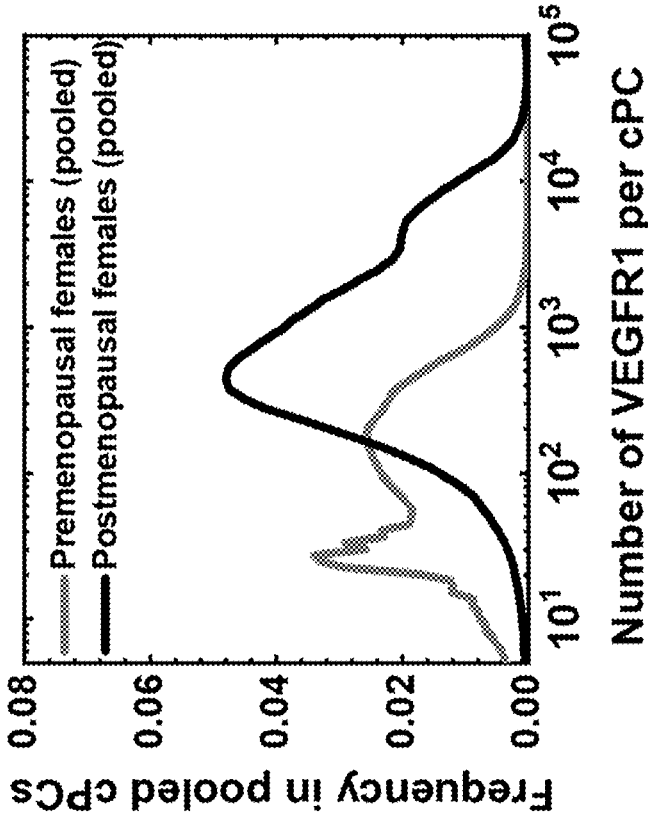
Figure 21:
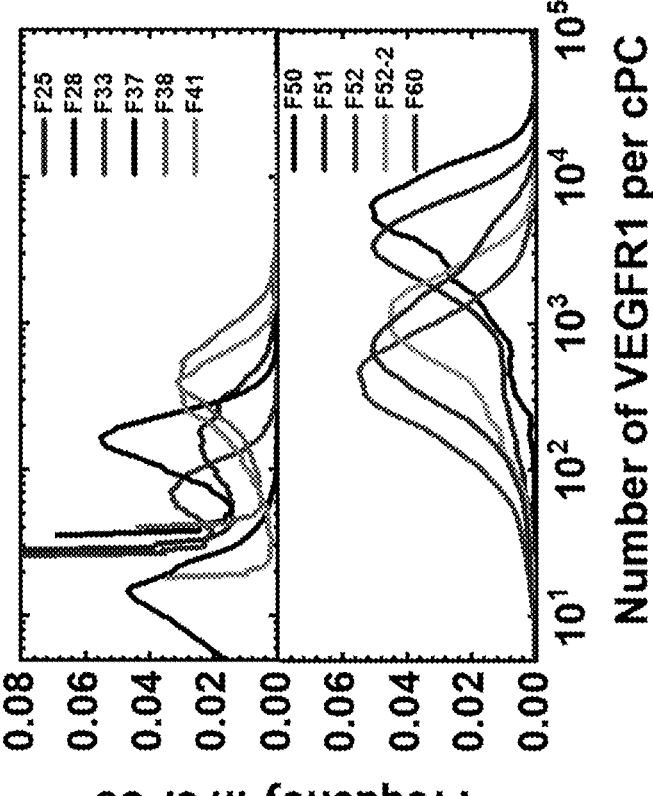

FIG. 21 shows cPCs of postmenopausal females generally present higher surface VEGFR1 concentrations that those of premenopausal females. (Left) VEGFR1 distributions in cPCs from individual female blood samples (10,000 cPCs per sample) are characterized cell-by-cell. (Right) Pooled VEGFR1 measurements represent the difference in the VEGFR1 distribution on cPCs between females over 50 y/o (postmenopausal, n=5) and females under 50 y/o (premenopausal, n=6). The medians of VEGFR1 concentrations are 88 VEGFR1s/cPC and 650 VEGFR1s/cPC in pooled premenopausal females and postmenopausal females, respectively.

FIG. 22/Table 2 shows descriptive statistics of VEGFR expression levels in each sex*age group. Blood samples are pooled based on sex*age interaction categories. Median and IQR values of VEGFR concentrations are extracted from the pooled cell-by-cell VEGFR distributions to represent the healthy levels of VEGFR1 and VEGFR2 on cECs and cPCs in these sex*age groups. * Indicates the values are below the previously established quantifiable threshold (500 VEGFR/ cell) [S. Chen 2017]. Values of VEGFR2 per cPC are not shown because they were all below the 500 VEGFR/cell threshold.

Figure 23A:
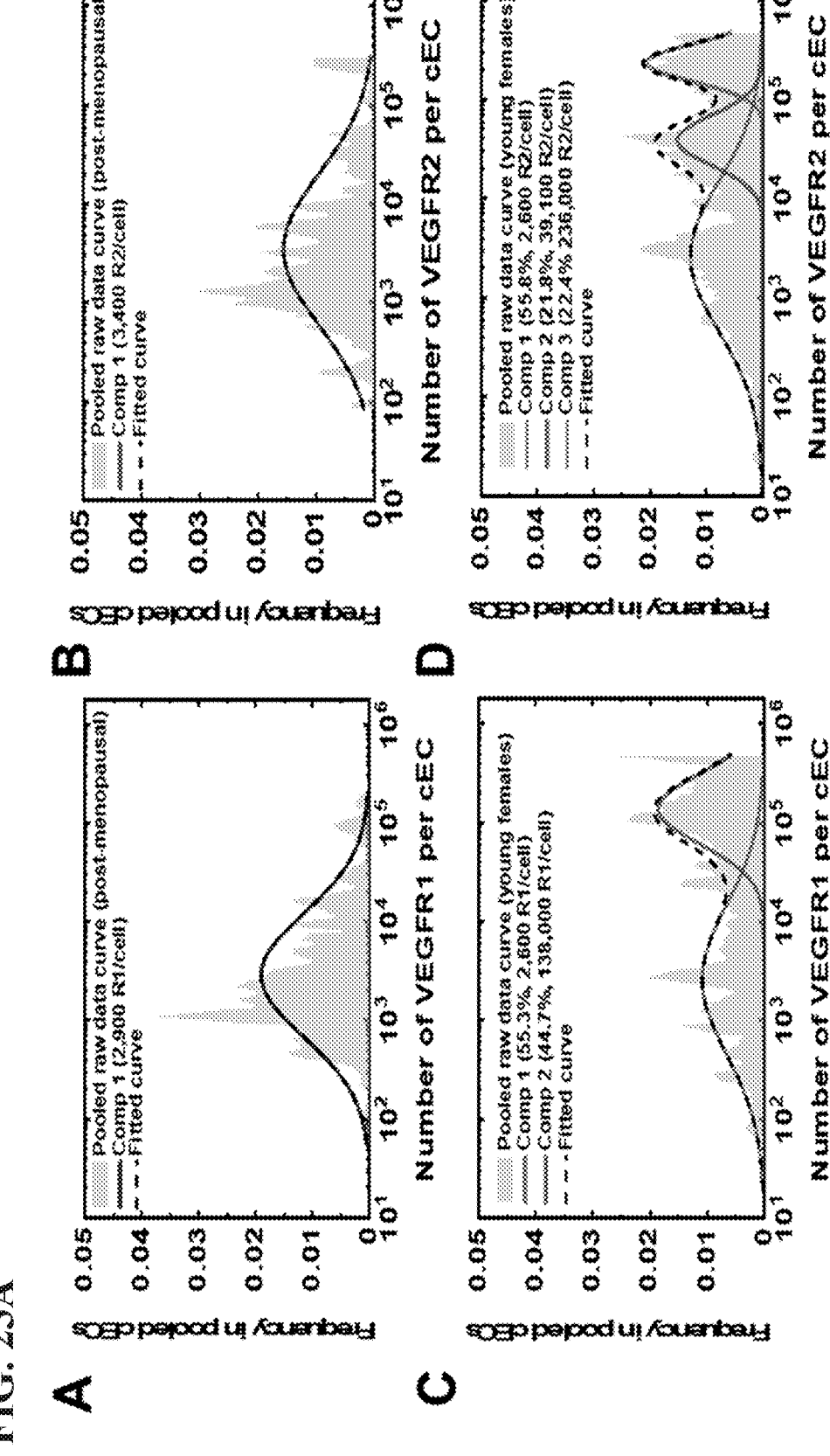
Figure 23B:
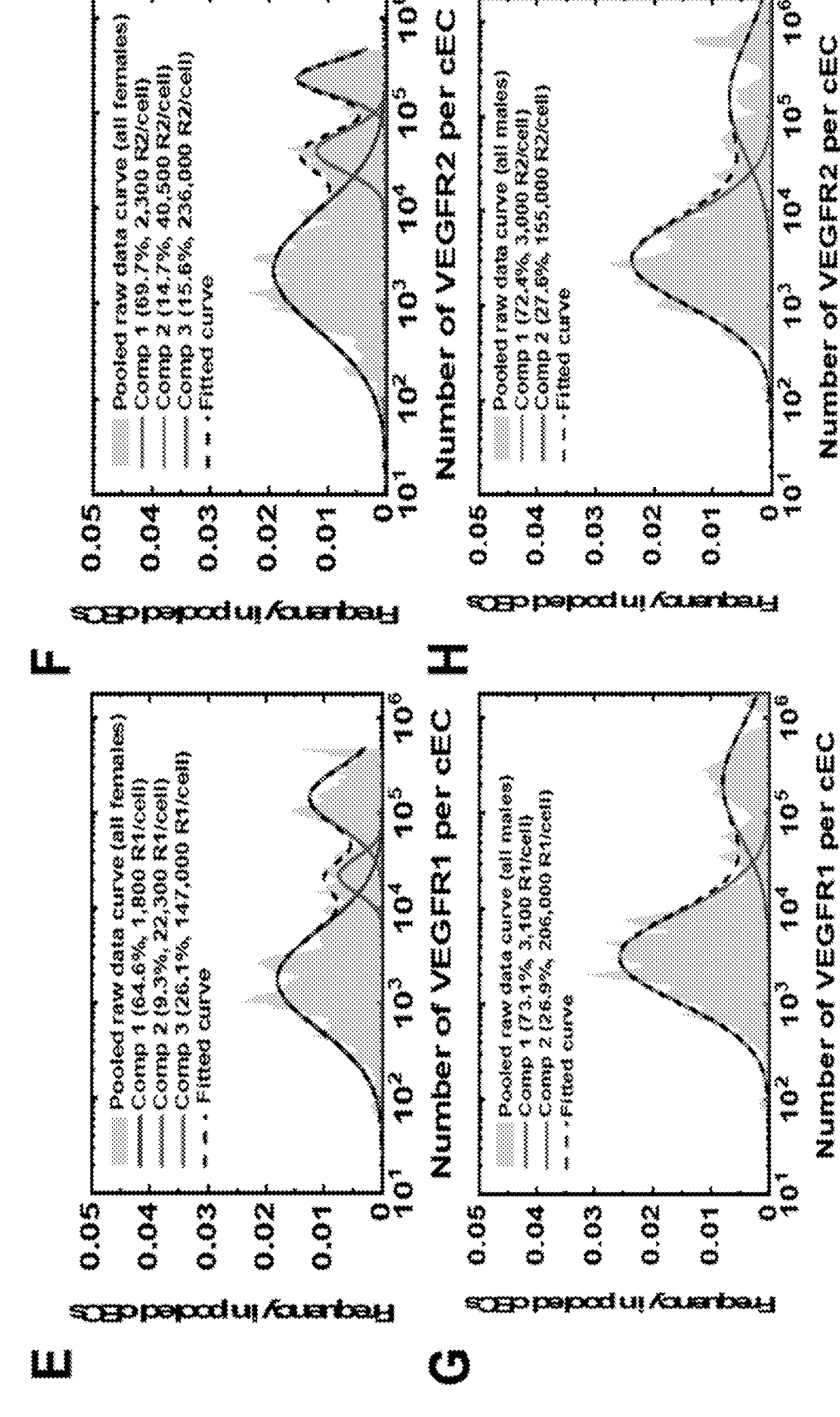

FIG. 23A and FIG. 23B show that premenopausal females have prominent VEGFR-high cEC subpopulations that post-menopausal females (50-60 y/o) lack; males in general have a smaller fraction of VEGFR-high cECs. Inspired by the age-specific differences in the averaged VEGFR concentrations on cECs, we separately pooled the VEGFR measurements from (A-B) post-menopausal females and (C-D) younger females to compare the VEGFR distributions between these two groups. (A-B) In postmenopausal females, cECs expressed 2,900 VEGFR1 and 3,400 VEGFR2 per cell (median of cell populations). (C) In premenopausal females, 44.7% cECs made up VEGFR-intermediate/high subpopulations that expressed 138,000 VEGFR1/cell (median). (D) The premenopausal females showed three cEC subpopulations based on median VEGFR2 concentrations: 55.8% cECs had 2,600 VEGFR1/ cell, 21.8% had 39,100 VEGFR2/cell, and 22.4% had 236, 000 VEGFR2/cell. (E) By pooling all the females (25-60 y/o), we identified three cECs subpopulations based on median VEGFR1 densities: 64.6% cECs had 1,790 VEGFR1/cell, 9.3% had 22,300 VEGFR1/cell, and 26.1% had 147,000 VEGFR1/cell; (F) and three cECs subpopulations based on median VEGFR2 densities: 69.7% cECs had 2,250 VEGFR2/cell, 14.7% had 40,500 VEGFR2/cell, and 15.6% had 236,000 VEGFR2/cell. (G) Since no age-related difference was statistically identified among males, we pooled cEC measurements from males of all ages and observed two cEC subpopulations based on VEGFR1 densities: 73.1% cECs had 3,100 VEGFR1/cell and 26.9% had 206,000 VEGFR1/cell. (H) We observed two cEC subpopulations based on VEGFR2 concentrations: 72.4% cECs had 3,000 VEGFR2/cell and 27.6% had 155,000 VEGFR2/cell.

Figure 24:
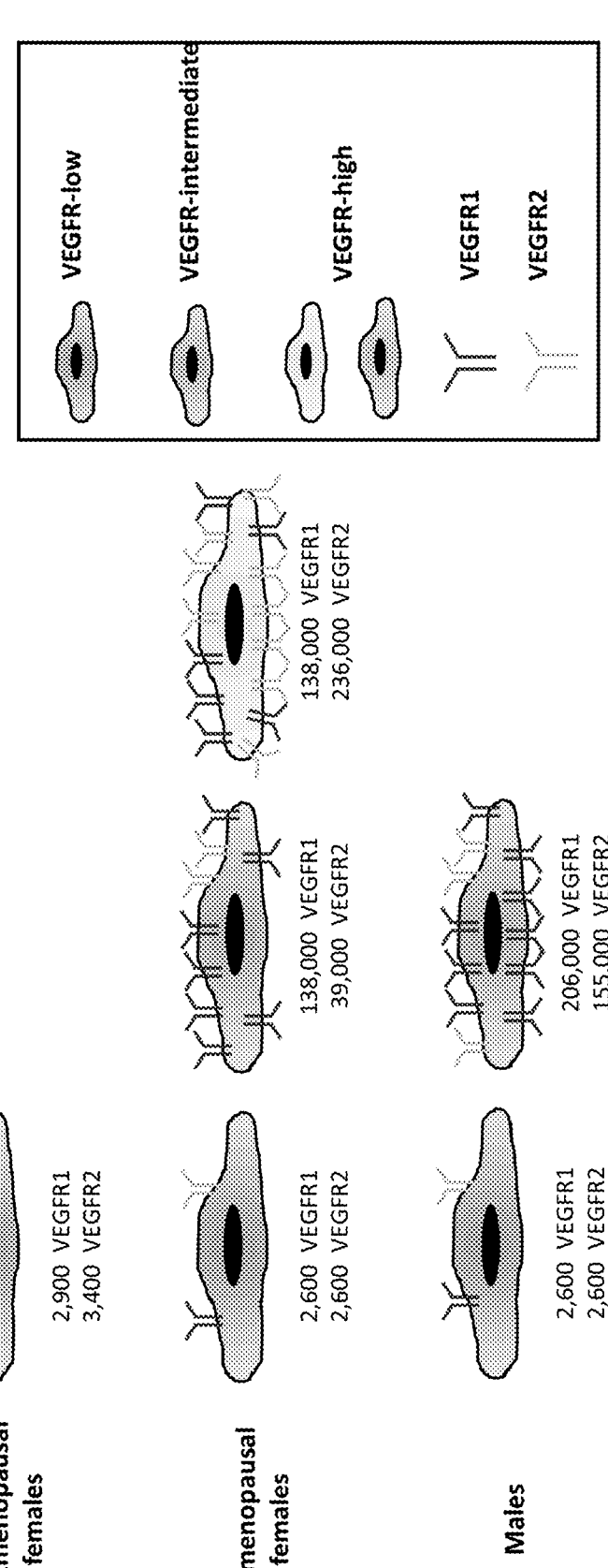

FIG. 24 is a plot of Hypothetical cEC subpopulations in healthy post-menopausal females, premenopausal females, and males. Postmenopausal females have relatively homogenous cEC populations that express lower VEGFRs compared to premenopausal females that have at least three cEC subpopulations (VEGFR-low, VEGFR-intermediate, and VEGFR-high). Males' cECs are mainly comprise a low-VEGFR subpopulation and a VEGFR-high subset.

DETAILED DESCRIPTION OF THE INVENTION

In general, the present invention is directed to methods for evaluating angiogenesis in a subject. Also provided are methods for evaluating the suitability of an anti-angiogenic therapy in a subject. In various embodiments, the subject is an obese subject.

In various embodiments, whether or not a subject is a suitable candidate for anti-angiogenic therapy depends on the levels of tyrosine kinase receptors on certain cell populations in the adipocyte or peri-adipocyte tissue. In additional embodiments, the therapeutically effective dose of an anti-angiogenic therapy may depend on levels of the tyrosine kinase receptors on the cell populations. For instance, elevated levels of tyrosine kinase receptors may require lower doses of the anti-angiogenic therapy while lower levels of the tyrosine kinase receptors may require higher doses of the therapy. Provided herein are methods of isolating relevant cell populations in obese subjects (e.g., from the stromal vascular fraction) and methods for quantifying an angiogenic tyrosine kinase receptor (i.e., the vascular endothelial growth factor receptor or VEGF receptor) on specific cell populations obtained from the subject. In various embodiments, the specific cell populations can comprise endothelial cells (including circulating endothelial cells), adipose tissue inflammatory cells (e.g. activated T lymphocytes and macrophages), endothelial progenitor cells, myeloid progenitor cells, blood cells (e.g. monocytes), and preadipocytes. Methods for isolating the specific cell populations listed herein are also provided. Additional embodiments are described herein.

Methods of Evaluating Angiogenesis in a Subject

In various embodiments, a method of evaluating angiogenesis in a subject having or at risk of developing obesity is provided. The method comprising: (a) isolating a stromal vascular fraction (SVF) in an adipocyte tissue sample obtained from the subject; (b) isolating a subpopulation of cells from the SVF using flow cytometry (c) quantifying VEGFR expression on the cell fractions; and (d) determining an amount of angiogenesis occurring in the subject based on the levels of VEGFR expression on the surface of the cell subpopulation. The adipocyte tissue sample can be derived from visceral and/or subcutaneous adipose tissue.

Methods of Determining Suitability of an Anti-Angiogenesis Treatment in an Obese Subject.

Also provided is a method of determining the suitability of an anti-angiogenesis treatment in an obese subject comprising (a) isolating stromal vascular fraction (SVF) from an adipocyte tissue sample obtained from subject; (b) isolating a subpopulation of cells from the SVF using flow cytometry; (c) quantifying levels of VEGF receptors on cells; and (d) identifying the subject as a candidate for anti-angiogenesis treatment if the levels of VEGF on the isolated subpopulation of cells exceed a threshold. The adipocyte tissue sample can be derived from subcutaneous adipose tissue.

In any embodiment described herein, the subpopulation of cells referenced herein is selected from the group consisting of adipose tissue myeloid progenitor cells, endothelial cells, blood cells, endothelial progenitor cells, preadipocytes, blood cells, and "other". Likewise, the adipocyte tissue sample can be derived from visceral and/or subcutaneous adipose tissue.

In additional embodiments, labeling the CD34(+) cells (step (b)) may further comprise (i) labeling cells in the SVF with cell markers against CD31, CD45, F4/80, and CD146 (ii) isolating CD31+CD146+CD45+F4/80+ cells as adipose myeloid progenitor cells; CD31+CD146+CD45− cells as endothelial cells, CD31+CD146−CD45+ as blood cells, CD31+CD146−CD45− as endothelial progenitor cells, CD31−CD146−CD45− as preadipocytes and CD31−CD146−CD45+ as other unclassified cells.

Figure 15:
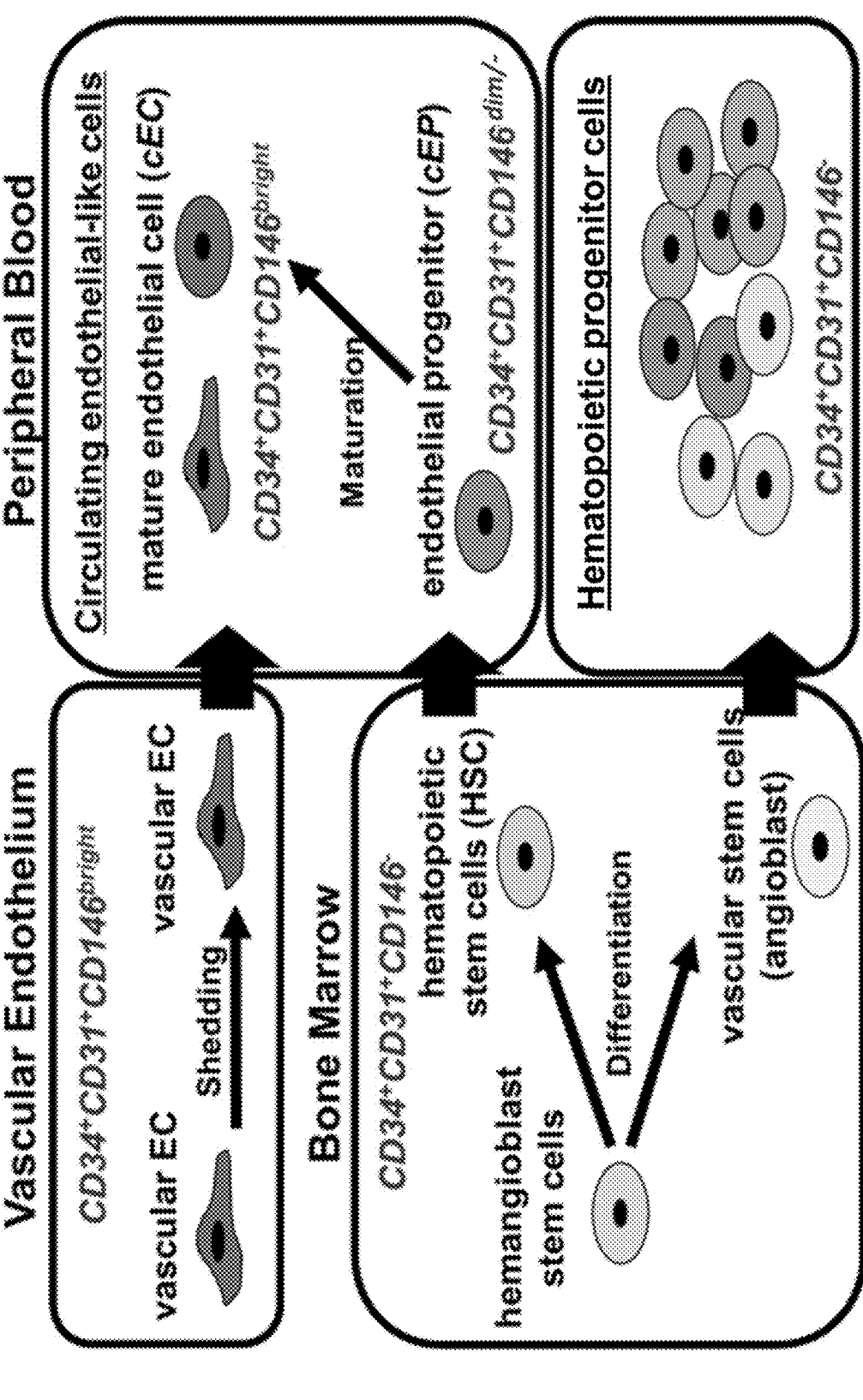
FIG. 15 diagrams the development of circulating endothelial cell-like cells and their markers. The co-expression of CD34 and CD31 is a specific immunophenotypical marker of circulating endothelial cells and bone marrow-derived progenitor cells, all of which have shown functional involvement in systemic angiogenesis. These CD34+CD31+ cells are isolated from peripheral blood, and defined as circulating progenitor cells (cPCs). The addition of endothelial marker CD146 identifies putative circulating endothelial cells (cECs), including both circulating vascular endothelial cells (cVECs) and possibly bone marrow-derived circulating endothelial progenitor cells (cEPCs). The rest of CD146–

In further embodiments, labeling the CD34+ cells may comprise labeling cells in the SVF or blood sample with cell markers against CD31, CD45, and CD146 and isolating $CD34^+CD31^+CD146^-$ as blood progenitor cells (e.g., bone marrow-derived hematopoietic progenitor cells); and isolating $CD34^+CD31^+CD146^+$ as circulating endothelial cells (such has those shed from blood vessels). See FIG. 15.

Methods of Quantifying VEGF Receptors on Cells

The methods described herein can further comprise quantifying VEGF receptors on an isolated cell population. Preferably, the VEGF receptors are quantified using quantitative flow cytometry.

In embodiments, the quantitative flow cytometry (particularly when used to analyze stromal vascular fractions) can further comprise a) a cell-by-cell analysis of the stromal vascular fraction measuring a plurality of VEGF receptors for individual cells, thereby obtaining a VEGF receptor profile for one or more subpopulation of cells from the stromal vascular fraction, wherein said VEGF receptor profile parameters include concentrations of a plurality of plasma membrane VEGF receptors and, optionally, concentrations of one or more free plasma membrane VEGF ligands; b) determining a cell heterogeneity parameter characterizing the subpopulation of cells by applying a Bayesian Information Criterion model to analyze the VEGF receptor profile; and c) comparing the cell heterogeneity parameter to one or more cell heterogeneity reference values, thereby obtaining a classification of the cells with respect to the effectiveness of the anti-angiogenesis therapy.

In various embodiments, the methods can comprise applying a Bayesian Information Criterion model to analyze a Gaussian mixture model comprising 1-9 log-normal Gaussian sub-distributions. The Bayesian Information Criterion model can be used to select the Gaussian mixture model with the lowest Bayesian Information Criterion.

The cell-by-cell analysis of the SVF cell population can also be carried out using one or more techniques selected from the group consisting of flow cytometry, surface plasma resonance and computational modeling.

In addition, quantifying VEGF receptors can comprise using Quantibrite™ PE calibration beads to translate a mean PE fluorescence intensity value to the absolute quantity of PE molecules per cell, wherein the number of PE molecules per cell is proportional to the number of VEGF receptors per cell.

The methods described herein can further comprise treating the subject identified as a candidate for anti-angiogenic therapy with an anti-angiogenic therapy. The anti-angiogenic therapy can comprise an anti-VEGF drug.

Methods of Isolating Different Cells from a Blood Sample

Also provided is a method for isolating different cell populations from a blood sample, the method comprising: (a) isolating $CD34^+$ cells from the blood sample; (b) labeling the $CD34^+$ cells with cell markers against CD31 and CD146; (c) isolating $CD34^+CD31^+CD146^-$ as blood progenitor cells; and (d) isolating $CD34^+CD31^+CD146^+$ as circulating endothelial cells.

Also provided is a method of isolating different cell populations from a blood sample, the method comprising: (a) isolating $CD34^+$ cells from the blood sample; (b) labeling the $CD34^+$ cells with cell markers against CD31 and CD146; (c) isolating $CD34^+CD31^+CD146^-$ as blood progenitor cells; (d) isolating $CD34^+CD31^+CD146^+$ as mature endothelial cells; and (e) isolating $CD34^+CD31^+CD146^{dim}$ as endothelial progenitor cells.

The circulating endothelial cells can comprise cells shed from blood vessels. The blood progenitor cells can comprise bone marrow-derived hematopoietic progenitor cells.

The method can further comprise quantifying VEGF receptors on at least one of the isolated cell populations. This step of quantifying VEGF receptors can further comprise quantitative flow cytometry, as described above with minor adjustments. Specifically, the quantitative flow cytometry comprises a) a cell-by-cell analysis of blood cells measuring a plurality of VEGF receptors for individual cells, thereby obtaining a VEGF receptor profile for one or more subpopulation of cells from the blood cells, wherein said VEGF receptor profile parameters include concentrations of a plurality of plasma membrane VEGF receptors and, optionally, concentrations of one or more free plasma membrane VEGF ligands; and b) determining a cell heterogeneity parameter characterizing the subpopulation of cells by applying a Bayesian Information Criterion model to analyze the VEGF receptor profile.

The method of analyzing VEGF receptors on blood cells, can further comprise using Quantibrite™ PE calibration beads to translate a mean PE fluorescence intensity value to the absolute quantity of PE molecules per cell, wherein the number of PE molecules per cell is proportional to the number of VEGF receptors per cell.

In further embodiments, CD34+ cells may be isolated using magnetic beads. For example, FIG. 16A and FIG. 16B outlines a representative protocol for isolating CD34+ cells in a blood sample. Non-RBC cells are incubated with desthiobiotinylated (DSB) anti-AD34 antibodies. Streptavidin-coated magnetic beads are then added and allowed to interact with the antibodies. The magnetic beads are then collected to enrich for a CD34+ population, which is then disassociated from the beads.

Systems Biology for Angiogenic Interventions for Obesity

Angiogenic Biomarkers are Needed for Obesity Therapy

Worldwide, obesity has nearly tripled since 1975, affecting over 650 million adults (World Health Organization). Obesity, chronic inflammation accompanied by hallmarks of pathological angiogenesis, not only compromises quality of life but also increases the risk of such life-threatening diseases as cardiovascular diseases, stroke, type 2 diabetes, and certain cancers. Current treatments for obesity are limited to non-pharmacological management, such as diet and lifestyle changes, physical exercise, and surgical procedures. Effective pharmacological treatments are urgently needed.

Impaired angiogenesis in adipose tissues contributes to obesity and accompanying inflammation. Adipose tissue is highly vascularized: each adipocyte is enriched by capillaries that supply nutrients, oxygen, cytokines, growth factors, circulating stem cells, and inflammatory cells. Nutrients and oxygen support adipocyte maintenance, cytokines and growth factors control adipocyte mass and function, recruited circulating stem cells and inflammatory cells augment adipogenesis, and the interplays between adipocytes and vascular endothelium promote pre-adipocyte differentiation.

A substantial amount of data supports the concept of the adipose tissue vasculature as a source of new targets for treating obesity and related diseases. Vascular endothelial growth factors (VEGFs) and their classic receptors (VEGFRs) are the most important mediators of angiogenesis; according to the Genotype-Tissue Expression (GTEx) database, adipose tissue is one of the highest VEGF and VEGFR gene-expressing tissues. Adipose tissue expansion is regulated and limited by its vascular supply. Impaired adipose tissue angiogenesis is a contributing factor to obesity and the accompanied inflammation. Anti-angiogenic therapies could regress pathological angiogenesis by reducing the amount of available VEGFs or VEGFRs. Paradoxically, insufficient angiogenesis leads to adipose tissue hypoxia that worsens obesity-induced inflammation and triggers insulin resistance. In addition, emerging evidence has shown that specific types of obesity could contribute to anti-angiogenic drug resistance in cancer therapy. However, little is known about the system of pro- and anti-angiogenic components in adipose tissue, so the molecular mechanisms for obesity-associated anti-angiogenic resistance remain poorly understood.

A significant predictor of anti-angiogenic efficacy in cancer therapy is VEGFR expression by tumor cells. High VEGFR1 membrane concentration could lead to therapeutic resistance to anti-VEGF drugs, and a small increase of 1000 receptor/cell could double downstream signaling. For obesity treatment, the efficacy of angiogenic therapeutics on correcting VEGF-VEGFR signaling could be similarly affected by the concentrations of membrane VEGFRs in targeted tissues, which heterogeneously distribute on various cell types of different adipose depots and can vary between individuals. Quantitative flow cytometry (qFlow) combined with multi-parametric analysis allows absolute quantification of membrane receptor concentrations on cell types of interests. Our lab has advanced qFlow to capture the heterogeneous modulation of membrane angiogenic receptors on the single cell basis. We have applied qFlow to measure plasma membrane receptor levels within tumor xenograft tissues, mouse hypoxic skeletal muscle vasculatures, and in-vitro cell lines of endothelial cells, stromal cells, and macrophages. The obtained measurements of membrane receptors are accurate, reflective of true biological state, and extremely useful for parameterizing computational models that delineate angiogenic functions of the measured tissue-vascular microenvironments. The in silico prediction can be further tuned and improved by iterated experiments and clinical studies until it is validated to serve as a diagnosis or prognosis companion tool—this process of experimental and computational iteration is also known as systems biology.

Systems biology has contributed to the discovery of robust predictors of disease and clinical responsiveness. This predictive power has led systems biology to be used throughout the medical research process, from drug discovery up to validation by regulatory investigators. In the Food and Drug Administration's New Drug Application (NDA) process, it is necessary to submit pharmacokinetic data to predict drug safety and toxicity. This data can be predicted based on physiologically-based pharmacokinetic models, which has led to the consistent annual rise in these models for pharmacokinetic evidence in NDAs. Our approach and results will shed light on the need for systems biology in developing predictive therapy for obesity, and to illustrate the systems biology workflow in studying VEGFRs in obesity.

Figure 1:
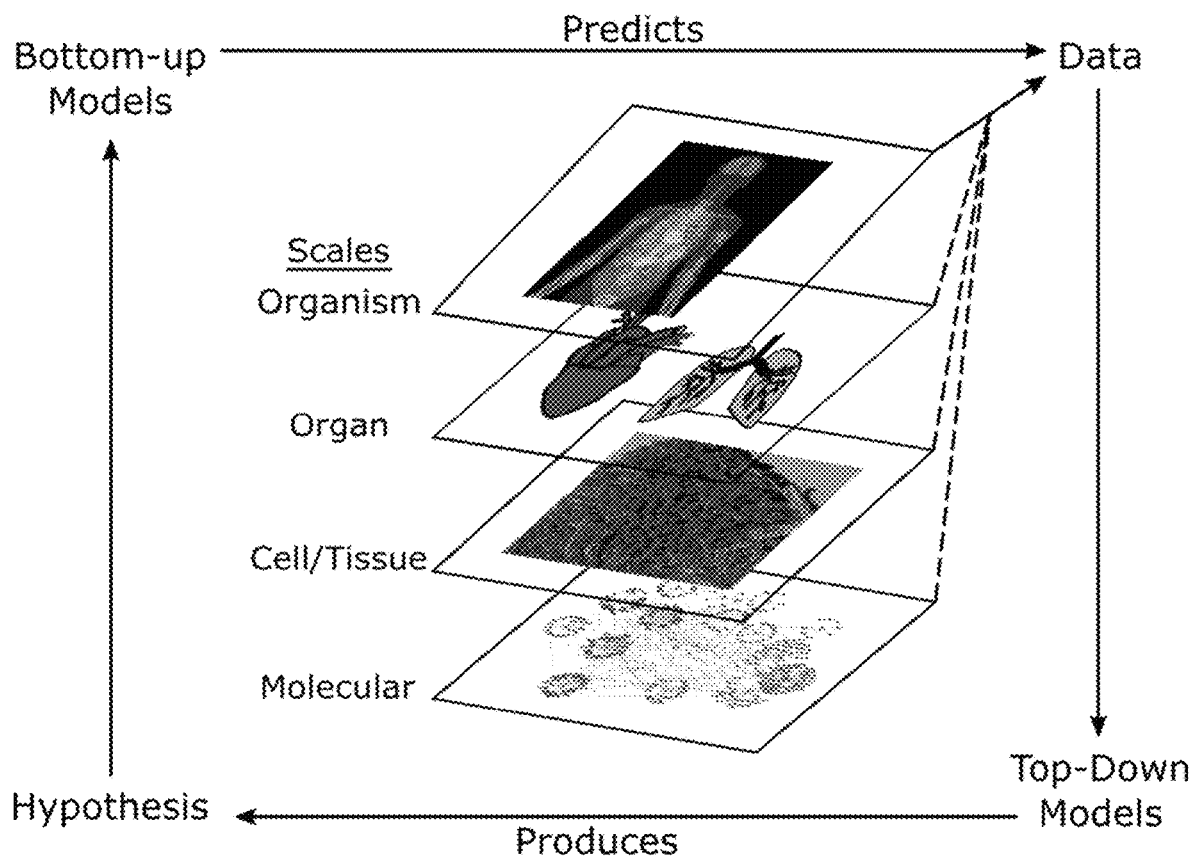
FIG. 1. Bottom-up vs. Top-down models and their targets. The data produced at multiple scales of biology is analyzed using top-down approaches. Bottom-up models are constructed using hypotheses, and are able to predict data.

Computational models are broadly defined as top-down or bottom-up. Top-down models are inherently statistical approaches which analyze the data from a system to infer a dependency or relationship; this produces systemic knowledge (FIG. 1). Bottom-up models reconstruct a system piece-by-piece and simulate the behavior of the system by integrating systemic knowledge and data; this can be used to predict data (FIG. 1). This data can be validated experimentally and similarly analyzed to further produce systemic knowledge.

Computational models are further specialized for a specific input, output, and scale. This specificity is defined in the scope of a model at the beginning of the modeling process and guides the development of a model. The scope of a model typically includes the modules, scales, and target behaviors that are to be modeled.

The spatial and temporal scales of the mechanisms and phenomena being modeled is central to the modelling process (FIG. 1). Data must be feasibly accessible at every scale included in each module, both to construct the model and to validate the results. Additionally, there are tradeoffs to consider when modelling at multiple scales.

Modules are the sub-systems produced by an emergent behavior. At the molecular scale there are many pathways that converge, which can make modeling a convoluted process. What pathways are the most important, and which are best to be omitted? This is a challenging question, and there is no definite answer. However, it is best to start by building simpler models as these may be enough to produce predictive insights or can be used as a module within a subsequent model.

Finally, the target behaviors depend on the hypothesis being tested but can be either a direct measurement or a proxy for the hypothesis.

Research applying bottom-up models in obesity has been used to find metabolic differences between lean and obese subjects. This was done through Flux Balance Analysis (FBA), a type of bottom-up modeling that was purposed for studying mass flows in metabolic networks. This culminated into a highly-detailed reconstruction of the metabolic network of the human adipocyte, which was integrated with subject transcriptomic data to reveal these metabolic differences.

Obesity research utilizing bottom-up models has been almost completely limited to FBA, which uses constraint-based, deterministic methods to model the metabolism, and a compartment-based method to model multiple tissues. However, many modeling methods have been developed to address the different needs of researchers. Developing models using other methods would open obesity research to exploring new hypotheses. These methods can be broadly categorized into Interaction-based vs. Constraint-based vs. Dynamic, Deterministic vs. Stochastic, and Agent-based vs. Compartment methods. Choosing an inappropriate method can lead to inaccuracy or a lack of robustness, and so in this section we will review these modeling methods and explain which of these choices are appropriate for modeling VEGFRs in obesity.

Interaction-Based vs. Constraint-Based vs. Dynamic

Figure 2:
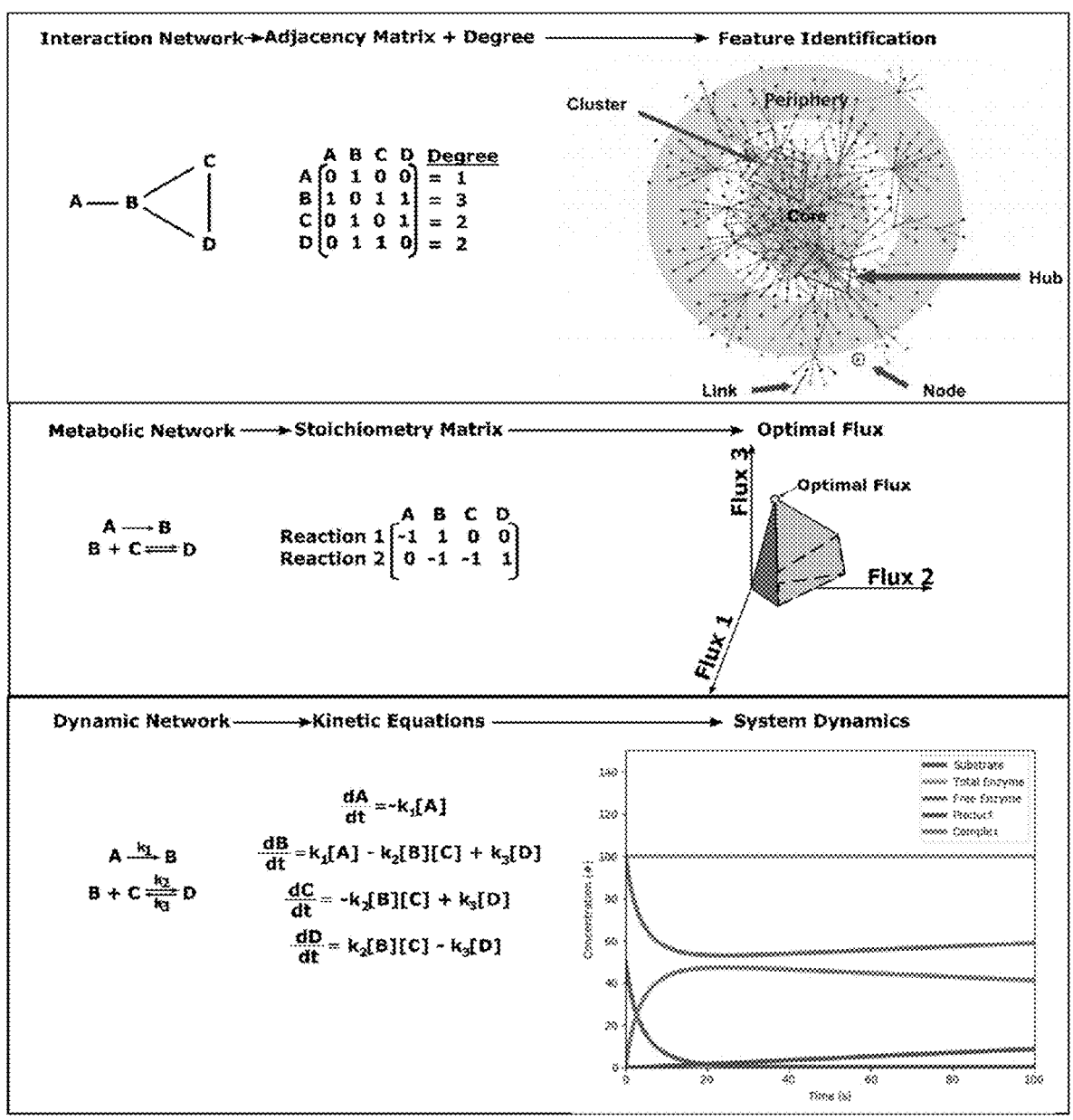
FIG. 2. Continuum of bottom-up models. The complexity of the representation is increased going from interaction-based to dynamic networks. Each can produce useful information.

Interaction-based, constraint-based, and dynamic methods are used to represent the interaction networks in a system (FIG. 2). In angiogenic research, dynamic methods are used to model VEGF/VEGFR activity over time and, in most cases, dynamic modeling methods are preferred for systems modeling. Dynamic methods incorporate the greatest amount of information and are robust predictors of system behavior because they include kinetic and regulatory behavior unlike interaction-based and constraint-based methods. However, the choice of using an interaction-based, constraint-based, or dynamic method depends on the objective of the modelling; an interaction-based method may be preferred when the scope involves identifying the function or validity of interactions and a constraint-based method may be preferred when the scope involves metabolomic information.

Interaction-based methods capture only the interactions without stoichiometry or dynamics. The analysis of interaction-based models follows from graph theory and is based on the network's topological features. Topological features such as connectedness can identify important nodes within the network which can lead researchers to identify essential molecules or interactions. Analysis at a higher-level can identify missing interactions and functionally similar molecules based on their topological 'fingerprint'. Interaction-based methods are helpful for revealing cellular and metabolic organization but cannot predict the function or behavior that will occur from a network.

Constraint-based methods add complexity by incorporating directionality and stoichiometry to the interaction network. The first constraint-based method was FBA for researching metabolic networks. Constraint-based methods are capable of modeling large, genome-scale networks. The entire network is expressed mathematically by a stoichiometry matrix, which encodes the stoichiometries of each metabolic reaction row-wise (FIG. 2). Traditionally, an objective function is defined by which targets specific metabolic reactions around which the network is optimized. Constraints are placed on input parameters, which changes the optimal value of the objective function. The maximum or minimum of the objective function is then calculated using linear programming. To ease the requirement of setting a user-defined objective function, Markov chain Monte Carlo methods (discussed later) sample many potential fluxes returning a distribution of potential optimal values. This also enables a more thorough exploration of the solution space. Constraint-based methods are able to predict the direction and variability of a network, which make them especially useful for genomic networks which are under normal circumstances in the same spatial compartment and not constrained by kinetics. Constraint-based methods, however, are not able to predict the outcome of an in vivo system which would impose regulatory control, e.g. proteomic networks, because the method does not incorporate kinetic parameters.

Dynamic methods encode interactions with their kinetic rate, providing the greatest level of detail. Dynamic methods include deterministic processes such as mass transport, mass generation, and mass clearance as well as stochastic processes such as mass aggregation and Brownian motion. Models that include molecular interactions utilize the law of mass action. Mass action is a simple mathematical extension of the stoichiometric equations used in FBA. Differentiating these equations over time establishes the rate at which the reactions take place. Dynamic processes can thus be mathematically expressed as kinetic equations (FIG. 2). Dynamic methods have been used in obesity research in physiologically-based pharmacokinetic models to model drug kinetics and for predicting the regulation of adipose tissue mass by hyperplasia or hypertrophy; however, there has been no development of models with molecular dynamics such as in VEGF/VEGFR signaling.

The largest difficulty in using dynamic methods to produce models is the large experimental burden associated with instantiating and validating these models.
Deterministic vs. Stochastic The traditional, mass action-based dynamic model is based on deterministic equations. Deterministic methods produce a fixed mapping from input to output and are useful because the model and hypotheses can be easily explored and validated. There has been extensive development of deterministic models in the field of angiogenesis for studying VEGFR activity in angiogenesis. These models advanced the understanding of the VEGF165b variant in peripheral artery disease, VEGF trapping in anti-angiogenic efficacy, and the signaling behavior of VEGFR1. These models are excellent examples of the analysis permitted by deterministic models. However, there are abundant stochastic processes in biology. Stochastic models are essential for modeling inherently non-deterministic processes but are also useful for inserting noise that one might expect in a biological system or for parameter sampling. Researchers seeking to implement a dynamic model in obesity should begin by using deterministic methods and use stochastic methods as needed.

Deterministic methods produce the same output for a given set of inputs. Every reaction leading from the input to the output is explicitly modeled and the data required to instantiate this model is based on concentrations and reaction rates. The dynamics of every molecule is accessible, and if they do not match with empirical validation then the parameters can be improved by parameter estimation methods. By iteratively invalidating the model, the accuracy and robustness will improve but a model cannot be necessarily "validated", in that a well fitted model is still not necessarily the best model. Deterministic models excel at exploratory modeling. Deterministic models can assess the impact of parameter uncertainty through sensitivity analysis, which modulates the value of each parameter over its range of uncertainty to determine how this impacts the predicted behavior. The straightforward validation procedure also makes deterministic modelling ideal for validating parameter estimates and hypothesized relationships.

Stochastic equation or algorithms have a random mapping from input to output which captures processes that are probabilistic. The output produced by stochastic method is a probability distribution rather than a fixed output, which will better represent non-deterministic processes or a range of possible outcomes. Stochastic models commonly simulate a Markov chain, which is a mathematical equation or algorithm that advances to the next state based only on the present state. Monte Carlo methods are usually used to construct the Markov chain, which perform repeated random sampling such that the simulated distribution or expected value approaches the theoretical distribution or expected value. Stochastic methods for biological modeling are mostly used and developed for biophysics applications, an example being the Gillespie algorithm which was specifically designed to simulate stochastic binding events between reactants in low concentration. Stochastic algorithms account for the uncertainty of biological systems unlike deterministic models which will simulate only the expected behavior. Stochastic models may produce more informative or faithful results compared to deterministic models because of this. The largest difficulty in using dynamic methods to produce models is the large experimental burden associated with instantiating and validating these models.
Agent-Based Vs. Compartment-Based Modelling at multiple scales is a challenge and is often necessary as several spatial and temporal scales contribute to an emergent behavior. Multi-scale models are essentially constituted by several single-scale models, but how to integrate single-scale models into a multi-scale model depends on the nature of the underlying biology. There are generally two strategies: discrete or continuum methods. The extensions of these methods for biological modeling are agent-based and compartment-based methods for the discrete and continuum methods, respectively. Both models have been used to great effect in angiogenic research. Agent-based models have been used to study angiogenic sprouting because of their ability to model unique cells. Endothelial cells were modeled as agents with heterogeneous profiles of Delta, Notch, and VEGFR2 which would interact with the Delta and Notch of other cells or with environmental VEGF-A gradients. Previous studies provided mechanistic insight into tip-stalk selection during sprouting, and recent advancements in high resolution imaging have allowed researchers to predict the site of initiation. Compartment-based models have been extensively used to study systemic anti-angiogenic pharmacodynamics, which is inaccessible by agent-based models. This allowed researchers to identify how serum and membrane levels of sVEGFR1/VEGFR1 can impact anti-angiogenic therapy.

Agent-based modeling uses the discrete method which represents each lower scale unit independently. Agent-based models are composed of agents with associated properties that interact with other agents and the environment. Agent-based models can define interactions by normal mass action kinetic equations but can also define rules-based interactions. Rules-based interactions are user-defined mathematical equations that describe state-switching or agent interaction. They are still defined by deterministic or stochastic equations. Rules-based interactions can greatly simplify the mathematics within the model, which is essential because the computational complexity of agent-based models can quickly increase.

Multi-compartment models are built with the continuum method use a mean-field approach to summarize lower scale behavior (FIG. 2). These models treat a tissue as the sum of a homogeneous assortment of cells. This creates a course resolution model that can capture essential system dynamics. Multi-compartment models are more common in practice, being the basis of the physiologically-based pharmacokinetic models and easily integrated with mass action kinetic equations in order to simulate pharmacodynamics as well.

There are several advantages and disadvantages to consider when choosing between an agent-based and multi-compartment approach. First, it is not feasible to use agent-based models to simulate cells at the whole organism scale because of the great computational complexity associated with simulating that number of unique cells; thus, a multi-compartment model must be used in this case. Second, agent-based models were designed to model heterogeneity while in the strict use of multi-compartment models, heterogeneity cannot be modeled. However, heterogeneity can be simulated in a multi-compartment model by using the Gillespie algorithm to sample the aggregate parameters in each compartment. This would suggest that either approach can be used regardless of heterogeneity, but there has been some disagreement between the outputs produced by the Gillespie compartment models and agent-based models. Additionally, this method is not applicable for modelling multiple cell types in the same compartment. Lastly, the rules-based modeling available in agent-based models allows for greater abstraction, which can simplify the modelling process. For studying the impact of VEGFR activity in obesity, an agent-based method is needed. Our scope includes 3 cells of interest in the adipose tissue, which cannot be modeled even by Gillespie compartment models. In addition, the precise effect of VEGFR2 activation on adipocytes is not known and so the rules-based modeling allows us to simulate how VEGFR2 activation is correlated with adipocyte proliferation.

Membrane VEGFR Concentrations are Biomarkers of Adipose Tissue Angiogenesis

Vascular endothelial growth factors (VEGFs) and their classic receptors (VEGFRs) are important mediators of angiogenesis. The human VEGF family consists of VEGF-A, VEGF-B, VEGF-C, VEGF-D, and placental growth factor (PlGF). VEGF-A binding to VEGFR1 and VEGFR2 represents the primary angiogenesis pathway. VEGF-A mediates angiogenesis through interaction with VEGFR2, leading to an increase in blood vessel formation through changes in endothelial proliferation, cellular permeability, and cell migration. Canonical angiogenesis theory describes VEGFR1 as a decoy angiogenic receptor, because it binds to VEGF-A with 10 times higher affinity than VEGFR2, and the resulting phosphorylation of VEGFR1 is much less efficient than that of VEGFR2. New insight has re-introduced VEGFR1 as a more complicated angiogenesis modulator, because it can lead to pro-angiogenic outcomes like cell proliferation, migration, and vasculature resistance to anti-VEGF drugs. Other known VEGF-VEGFR pathways include VEGF-B and PlGF interacting with VEGFR1; VEGF-C and VEGF-D interacting with VEGFR2; and VEGF-C and VEGF-D interacting with VEGFR3, which mainly regulates lymphogenesis. VEGFR3 is also expressed by endothelial cells and becomes up-regulated during angiogenesis.

Adipose tissue is one of the highest VEGF and VEGFR gene-expressing tissues, according to the Genotype-Tissue Expression database (GTEx). Higher VEGF and VEGFR expression levels contribute to greater angiogenic tendencies. Nevertheless, VEGFR gene expression might not always correlate with functional changes: for instance, the VEGFR2 mRNA level is downregulated in genetically obese mice but is not markedly modulated by nutritionally-induced obesity. It is also important to measure the protein expression of VEGFRs in adipose tissues.

VEGFR proteins are present on the plasma membranes of endothelial cells, macrophages, and certain stromal cells that are involved in adipose tissue expansion and angiogenesis. Adipocytes also possess VEGFR genes and proteins, examined by RNA-seq and immunohistochemistry, respectively (The human protein Atlas database). However, VEGFR protein measurements have never been performed for adipocytes.

Endothelial cells, the building blocks of angiogenesis, express all VEGFRs. The concentrations of membrane VEGFRs tightly regulate the balance of pro- and anti-angiogenesis of endothelial cells. For instance, the concentration of membrane VEGFR1 increases and VEGFR2 decreases on endothelial cells in vitro in a VEGF dose-dependent manner. Within tumor vasculature, high VEGFR1 membrane concentration is predicted, and clinically demonstrated to mark therapeutic resistance to the anti-VEGF drug, bevacizumab. A small increase of 1,000 receptors/cell on the plasma membrane could double the nuclear-based signaling of the receptor. Therefore, quantifying membrane VEGFR protein modulation in adipose tissue vasculature will help us better understand the role of VEGFRs in obesity and in the varied anti-VEGF drug responses observed in obese cancer subjects.

VEGFR1 and VEGFR3 are also found on macrophage membranes. Recruitment of adipose tissue macrophages is one of the hallmarks of obesity, and genetically obese mice have significantly higher adipose tissue macrophages content in their adipose tissues than wild type mice. Adipose tissue macrophages direct the inflammatory responses in obese adipose tissues: adipose tissue macrophages in lean mice are mostly M2 or "anti-inflammatory" macrophages, whereas adipose tissue macrophages in obese mice are predominantly M1 or "pro-inflammatory" macrophages. It is worth noting that the downregulation of VEGFR1 and VEGFR3 on macrophages accompanies upregulation of alternative angiogenic pathways, defeating anti-VEGF therapy. Therefore, quantification of VEGFR1 and VEGFR3 on adipose tissue macrophages will provide important insights into the links between inflammation and angiogenesis in obese adipose tissues.

Quantitative Flow Cytometry is a Powerful Tool for Finding Protein Biomarkers in a Complex Tissue Microenvironment We hypothesize that heterogeneity within the plasma membrane VEGFR levels in adipose tissue microenvironments can crucially influence angiogenic treatment responses. Our extended quantitative flow cytometry (qFlow) method generates quantitative analyses of both ensemble and cell-by-cell data. This allows accurate characterization of membrane receptor heterogeneity in adipose tissue microenvironments. Furthermore, qFlow, combined with multi-parametric analysis, allows absolute quantification of membrane receptor concentrations on cell types of interest.

To obtain quantitative VEGFR concentrations, we use QuantiBRITE™ PE calibration beads to translate the mean PE fluorescence intensity values to the absolute quantities of PE molecules per cell. The number of PE molecules per cell is conveniently equivalent to the number of VEGFRs per cell, due to the 1:1 protein/fluorescence binding ratio. Our lab has advanced the qFlow method to capture the heterogeneous modulation of membrane angiogenic receptors on a single cell basis. We have applied qFlow to measure plasma membrane receptor levels within tumor xenograft tissues, mouse hypoxic skeletal muscle vasculature, and in-vitro cell lines of endothelial cells, stromal cells, and macrophages. The obtained measurements of membrane receptors are accurate, reflective of true biological states, and extremely useful for parameterizing computational models that delineate the angiogenic functions of the measured tissue-vascular microenvironments. The resulting in silico predictions can be further validated by iterated experiments and clinical studies. Such validated predictions can offer new insights into diagnosis and/or prognosis. This process of experimental and computational iteration is also known as systems biology.

Systems Biology Translates Quantitative Biological Measurements into Insightful Computational Predictions Systems biology is a very attractive approach to translate complex cellular networks into simplified outputs. As the effectiveness of angiogenic therapeutics can be affected by the concentrations of membrane VEGFRs in targeted tissues, the heterogeneous VEGFRs distributions in obese adipose tissues is needed to better predict the outcomes of angiogenic therapies. Hence, systems biology is a very powerful approach for establishing a VEGFR-driven platform that predicts angiogenic therapeutics' effects on obese adipose tissues.

Having described the invention in detail, it will be apparent that modifications and variations are possible without departing from the scope of the invention defined in the appended claims.

EXAMPLES

The following non-limiting examples are provided to further illustrate the present invention.

Figure 3:
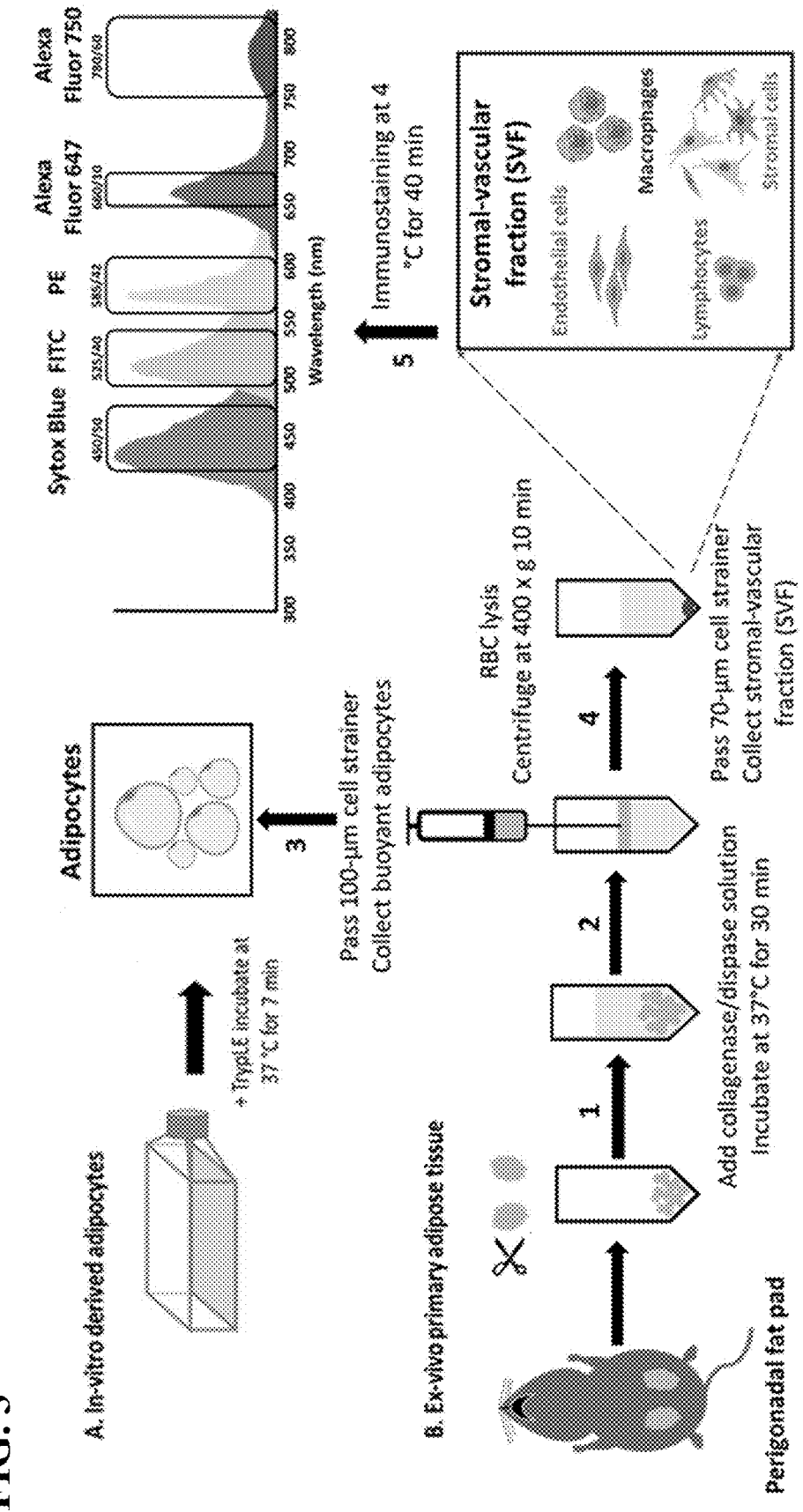
FIG. 3 depicts a procedure to prepare adipocytes and stromal-vascular fraction cells for quantitative flow cytometry analysis.
Figure 4:
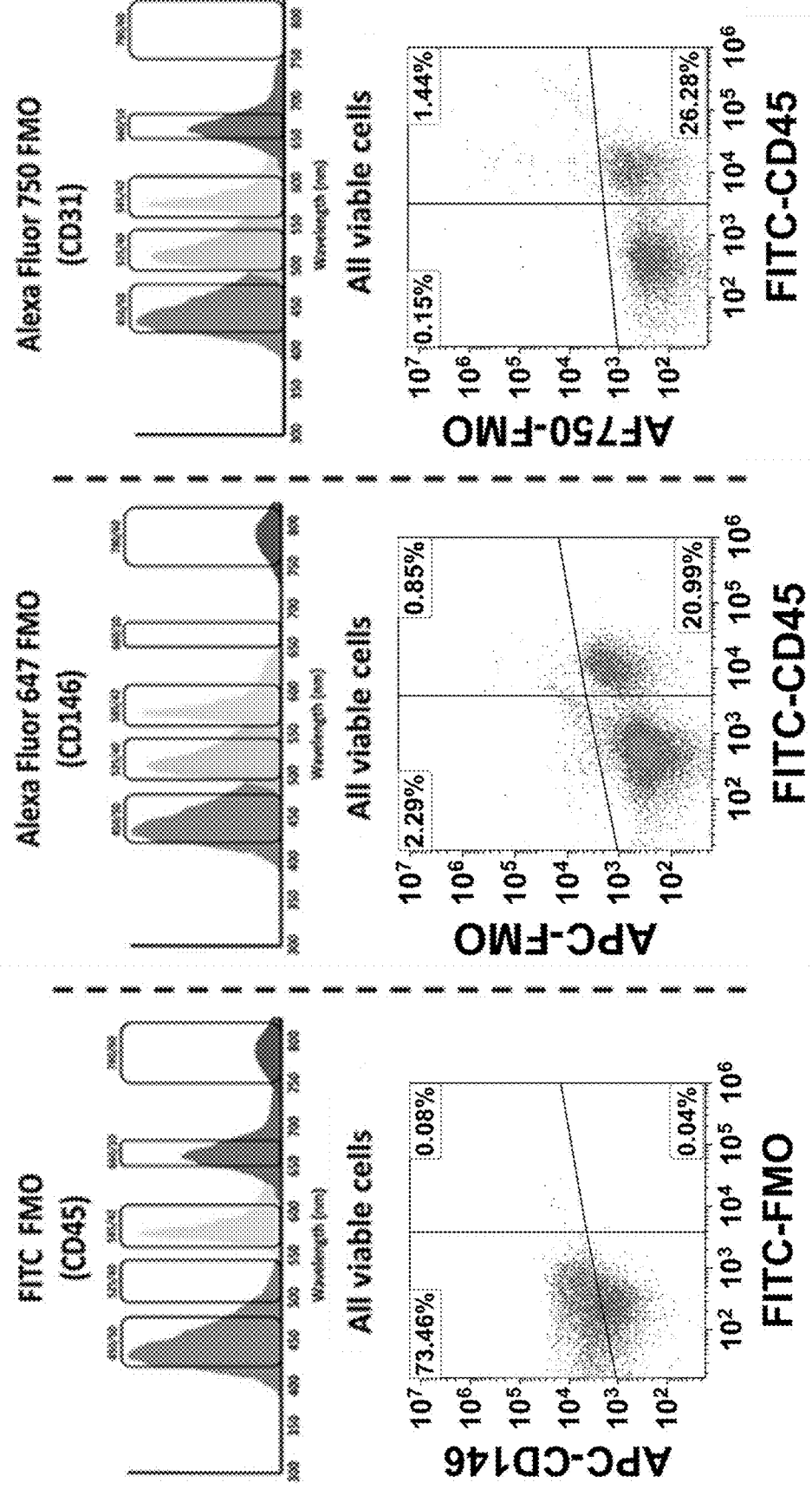
FIG. 4 depicts representative flow cytometry plots using a fluorescence minus one (FMO) control experiment. Plots are depicted below a diagram that indicates which signal was removed for each analysis. Discriminate positive versus negative signals using fluorescence minus one (FMO) controls. To ensure that any spread of the fluorochromes into the channel of interest is properly identified, FMO controls were set up by adding all fluorochromes except the one of interest in a panel.

Example 1: Quantitatively Describe Angiogenesis in the Adipose Tissue Microenvironment Via qFlow To optimize the qFlow protocol for primary adipose tissue analysis, we harvested adipose tissue samples from six C57BL/6 mice, 30-50 weeks old, on a normal chow diet and with little subcutaneous fat. We collected mainly visceral fat pads (perigonadal fat) for qFlow optimization (FIG. 3). Adipose tissue consists of adipocytes and the stromal vascular fractions (SVF). To identify the SVF cell types within the adipose tissue microenvironment, we labelled the mouse SVF cells with Alexa Fluor® 750-CD31, Alexa Fluor® 647-CD146, FITC-CD45, PE-VEGFRs, and the viability dye Sytox™ Blue. To ensure that any spread of the fluorochromes into the channel of interest was properly identified, fluorescence minus one (FMO) controls were set up by adding all fluorochromes except the one of interest in a panel (FIG. 4). OP9 is a stromal cell line from mouse bone marrow that can differentiate into adipocytes upon adipogenic stimuli in vitro. In-vitro derived OP9 mouse adipocytes were also examined for their membrane VEGFR concentrations.

Figure 5:
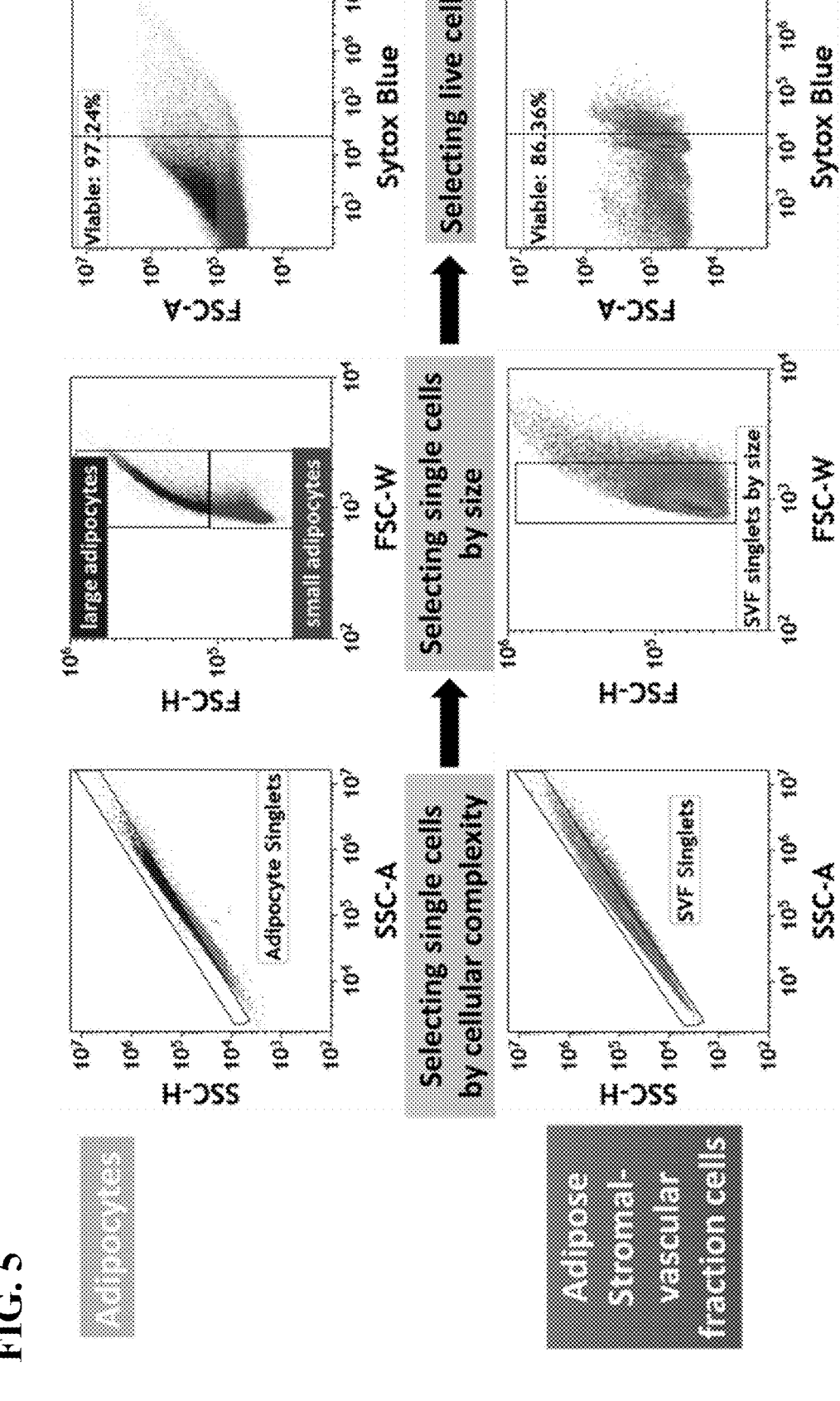
FIG. 5 shows mouse adipocytes and SVF size and viability selection. Single cells were selected based on the granularity parameter side scatter (SSC) and the size parameter forward scatter (FSC). For every signal passed into a detector, its height (H), width (W), and area (A) were recorded. Within scatter parameters, the area versus height and the width versus height were conventionally used to isolate single cells. Live cells were subsequently discriminated by the lack of expression of nucleic acid dye Sytox™ Blue.

A recent adipocyte flow cytometric study has highlighted the usefulness of flow cytometry for screening highly heterogeneous adipocytes at the single cell level. However, flow cytometric analysis with adipocytes remains challenging. Multiple caveats regarding using qFlow to quantify VEGFR levels on adipocytes must be considered, because adipocytes are large, fragile, and buoyant cells. To avoid breaking the adipocytes, we transferred adipocytes with P1000 micropipettes whose tips were enlarged by snipping. Adipocytes are hard to count: we estimated 2~4 million adipocytes/mL by slowly titrating adipocytes into 0.5 mL stain buffer until the color of the solution appeared cloudy, at which point adding more adipocytes would immediately result in a greasy top layer. This cell concentration of 2-4 million adipocytes/mL was confirmed by flow cytometry. To ensure effective antibody accessibility to cells, the adipocytes were incubated with antibodies for 40 min with gentle shaking every 5-10 min. To minimize lysis of the cells during cell washing, we used blunt PTFE needles to remove the subnatant, instead of transferring floating adipocytes to a new tube. For flow cytometry analysis, we used Beckman Coulter CytoFLEX™ flow cytometer that can measure cell sizes up to 180 μm diameter. The sheath pressure of the CytoFLEX™ was 3.6 psi and exerted very minimal shear stress on these fragile cells. Last but not least, we made sure that cells were well mixed into the solution immediately prior to flow cytometry screening. The size distribution and viability of the adipocytes and stromal-vascular fraction (SVF) cells harvested from mouse visceral fat depots are shown in FIG. 5. Both confocal images and flow cytometry screening have shown that the primary mouse adipose tissues encompass adipocytes of a broad range of sizes. Both large and small adipocytes possess nuclei, lipids, and cell membrane[51]. We grouped adipocytes into large and small subpopulations because cells with significantly larger surface areas would possess more membrane receptors (FIG. 5). The small adipocytes were of the similar size range as the adipose SVF population.

Figure 6:
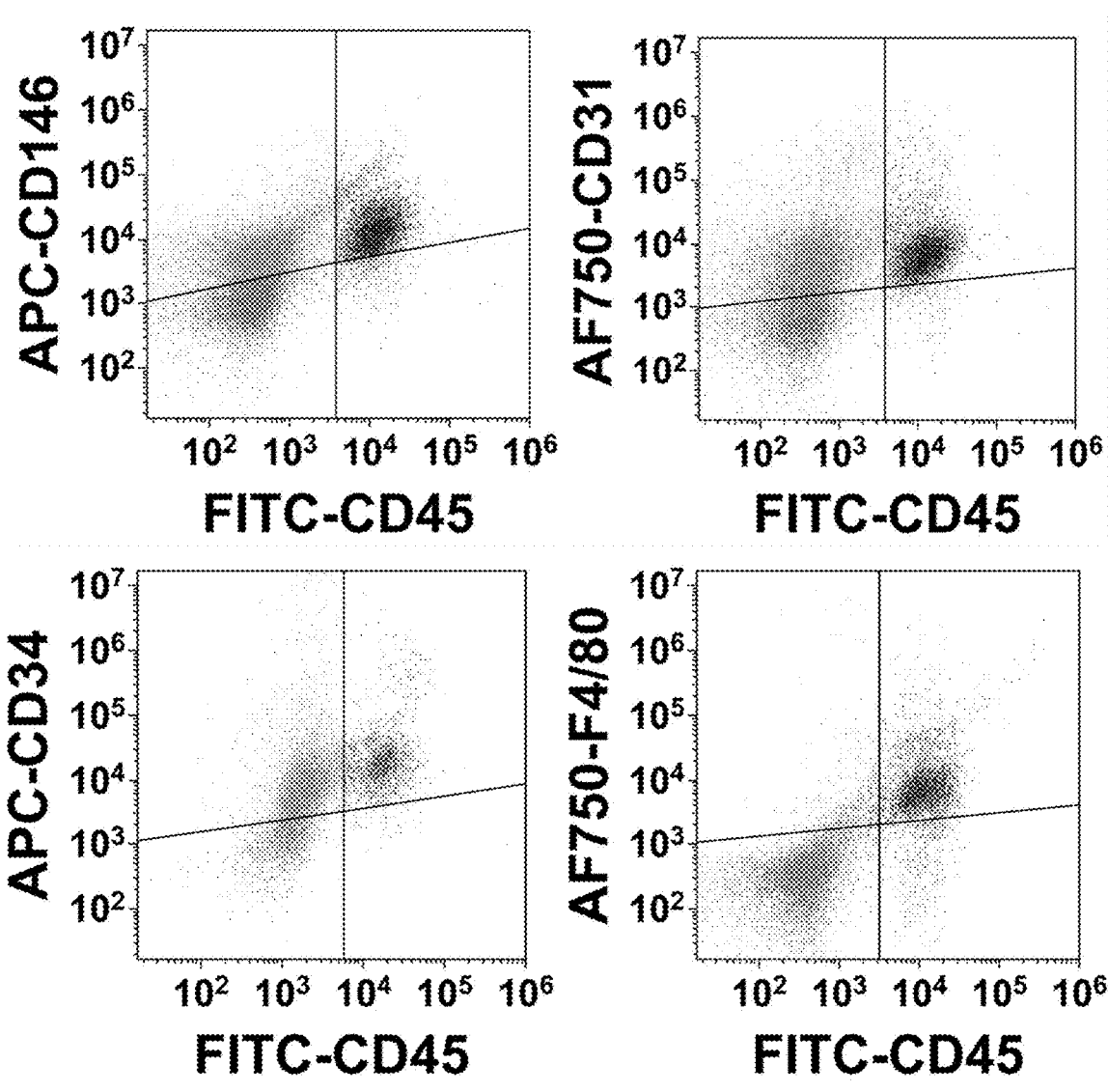
FIG. 6 is a diagram showing cell stratification of stromal-vascular fraction cells from mouse visceral fat depot. Grey populations are adipose endothelial cells which are CD146+ CD45–CD34+F4/80–. Blue populations are pro-angiogenic myeloid progenitor cells (MPCs) which are CD146+CD45+ CD34+F4/80+. The rest of the unstratified cells (grey) are a mixture of adipose stromal cells that mainly consist of fibroblasts and pre-adipocytes.
Figure 7:
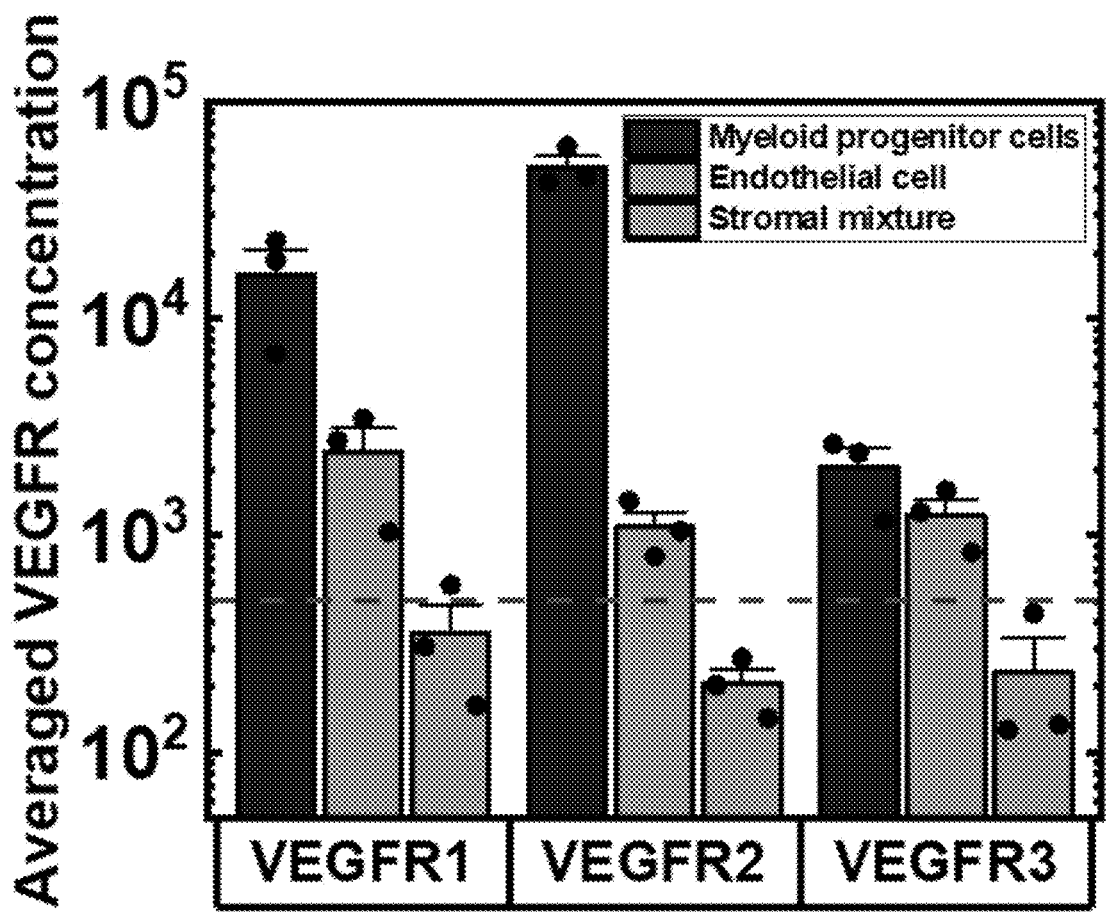
FIG. 7 shows membrane concentrations of VEGFRs (mean±SEM) of three SVF cell subpopulations isolated from mouse visceral fat depots as described in FIG. 6.

As shown in FIG. 6 endothelial cells were selected based on the classic CD31+CD146+CD45− phenotype. In the hematopoietic lineage (CD45+), CD146 is expressed on infiltrated macrophages and has a role in lipid uptake. We identified adipose myeloid progenitor cells as CD146+ CD45+ cells, which also express the stem cell marker, CD34, and the macrophage-specific marker, F4/80, suggesting the bidirectional potential of myeloid progenitor cells to become either endothelial cells or macrophages. Lastly, based on the previously reported phenotype, we putatively assigned the CD31−CD146−CD45− subpopulation to the stromal cell mixture. As a result, we found ~51% of the stromal vascular fraction were CD45−CD146+ endothelial cells and ~13% were CD34+CD45+CD146+F4/80+ adipose myeloid progenitor cells (FIG. 6), which was consistent with previously reported 17% F4/80+ myeloid progenitor cells in non-obese adipose tissue. In addition, a mixture of CD45− CD146− stromal cells, which contained fibroblasts and pre-adipocytes, comprised ~34% of the entire stromal vascular fraction. Lastly, we observed minimal CD45+CD146− lymphocytes (0.1-2%) in all lean mouse visceral adipose tissue samples. After identifying the subtypes of stromal vascular fraction, we performed qFlow analysis on each subtype as described to quantify the membrane VEGFR distributions within these cells, with ensemble-averaged results shown in FIG. 7, which shows the ensemble averages of membrane VEGFR concentrations on the SVF cells isolated from eleven mice in 3 experiments. We identified that adipose tissue had the following quantities of VEGFRs on their endothelial cell membranes: 2,400±710 VEGFR1/cell; 1,100±190 VEGFR2/cell; and 1,200±220 VEGFR3/cell (mean±SEM, n=3). The VEGFR1 and VEGFR2 concentrations on adipose endothelial cells are comparable to those of endothelial cells isolated from mouse skeletal muscle: 2,000-3,700 VEGFR1/cell and 1,300-2,000 VEGFR2/cell. The VEGFR3 concentration on adipose endothelial cells is about half of that on HUVECs, 2800±400 VEGFR3/cell, while data on VEGFR3 on ex-vivo endothelial cells are not available from the literature. On average, myeloid progenitor cells present 16,000±4,700 VEGFR1/cell, 50,000±6,200 VEGFR2/cell, and 2,100±460 VEGFR3/cell (mean±SEM, n=3).

Figure 8:
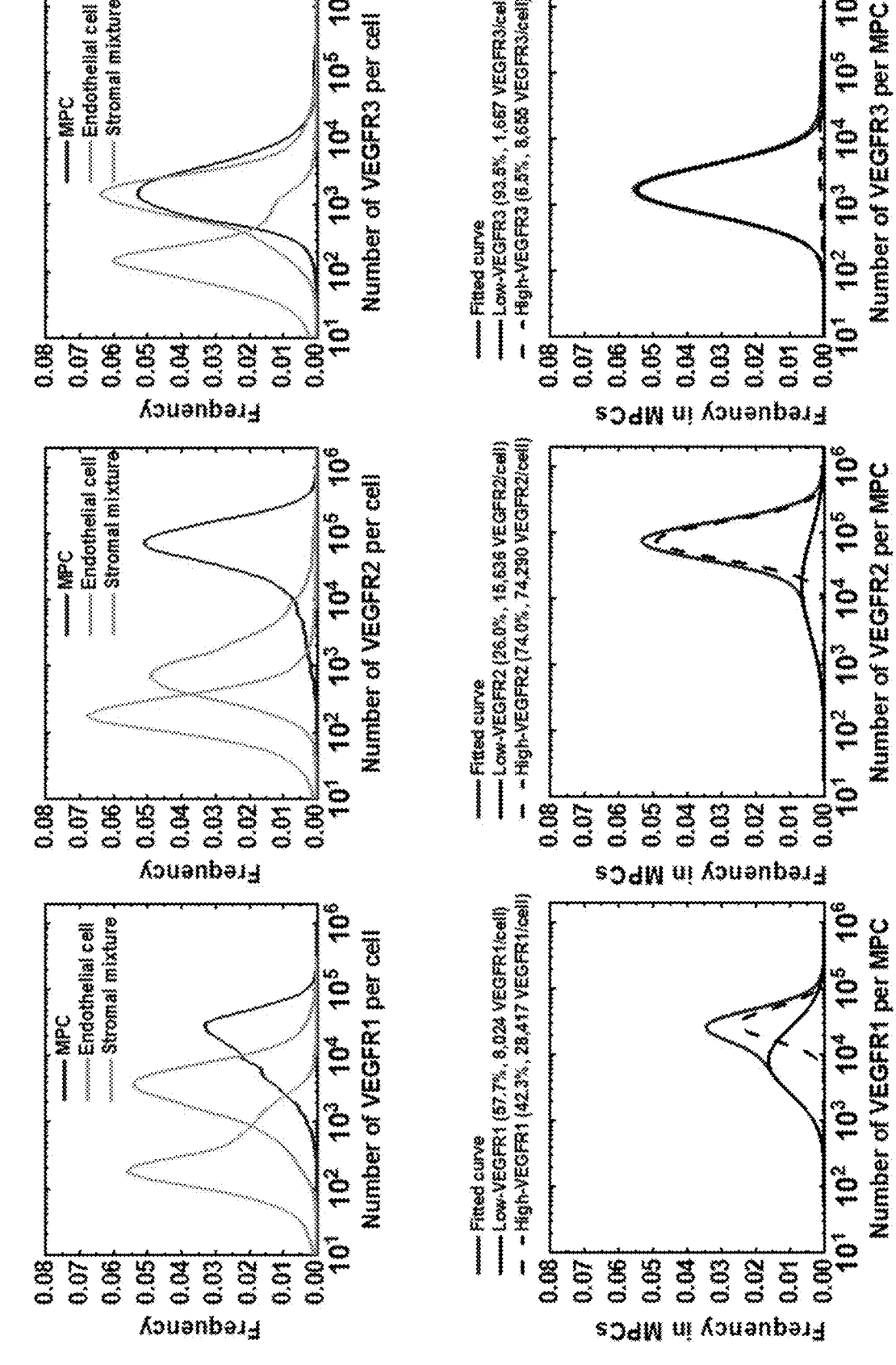
FIG. 8 top panels show heterogeneous cell-by-cell VEGFR distributions within adipose tissue-derived cell types from non-obese mouse visceral fat depots. The bottom panels show Bayesian information criterion (BIC)-assisted Gaussian mixture modeling, which identified subpopulations within the CD146+CD45+CD34+(F4/80+) myeloid progenitor cells. In comparison to VEGFR1 and VEGFR2, the VEGFR3 is a good representation of a homogenous distribution.

Example 2: Quantitative Cell-by-Cell Approach for Characterizing Adipose Tissue Heterogenity To characterize the cell-by-cell heterogenity of membrane VEGFR concentrations, we pooled single-cell VEGFR measurements from independent trials (FIG. 8). Due to the previous finding that VEGFRs best fit lognormal distributions, we chose the geometric mean (GM) of the membrane VEGFR concentrations as the best heterogeneous data representation for the pooled datasets.

Figure 11:
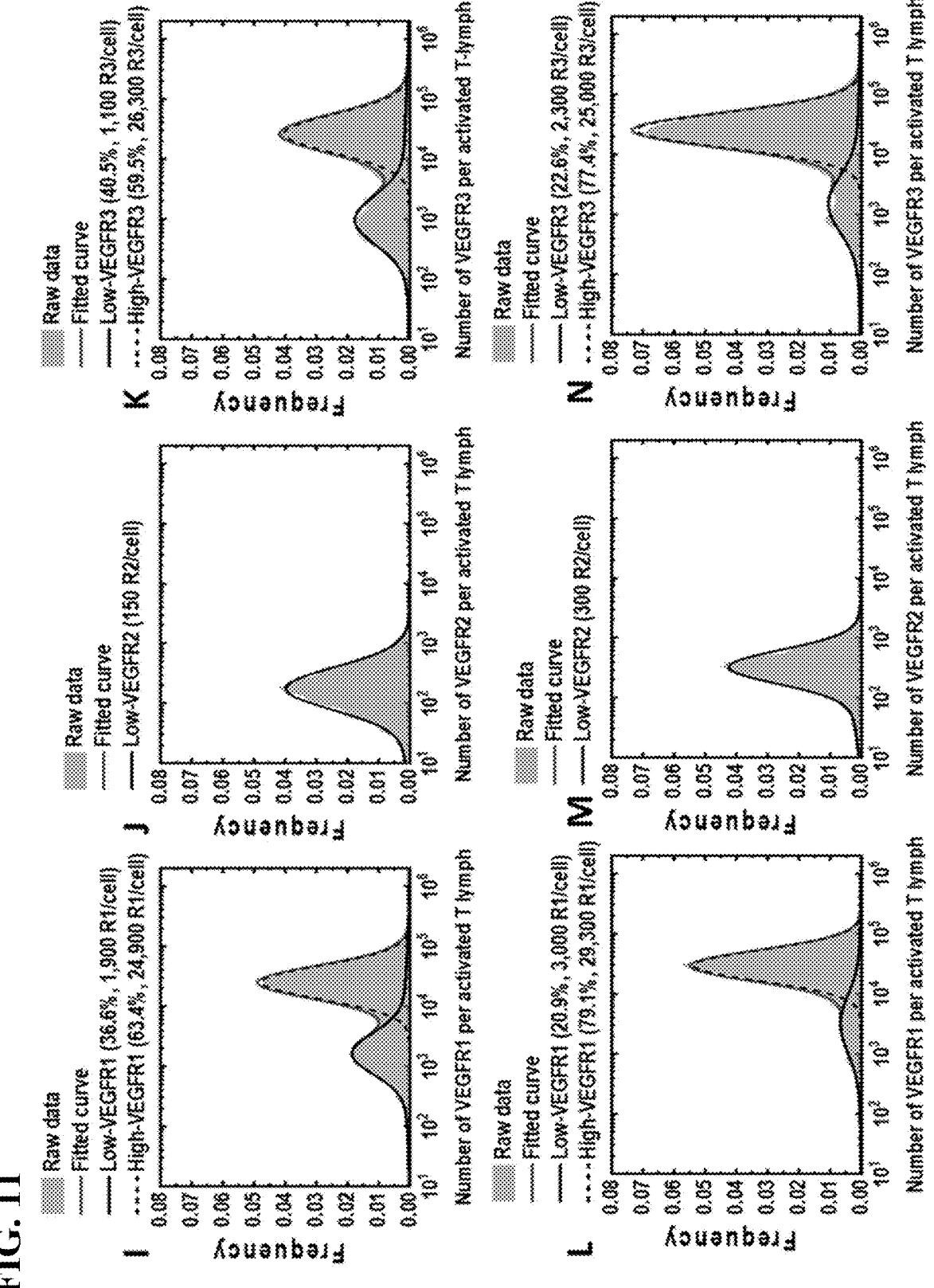
FIG. 11 shows Bayesian information criterion (BIC)-assisted Gaussian mixture modeling identified subpopulations within the human adipose tissue activated T lymphocytes from upper and lower body fat depots.

Although qFlow studies commonly report the population mean, the mean value can mask population heterogeneity because specific subpopulations can depart from the "mean" behavior. To identify and characterize such subpopulations, we performed a two-step data analysis: (1) fitting the VEGFR population distribution to log-normal distributions using mixture modeling (FIG. 8) and (2) applying Bayesian information criterion (BIC) to identify the number of subpopulations without overfitting (FIG. 11). We chose BIC over Akaike information criterion (AIC) because AIC can report false-positive subpopulations in qFlow data, increasing mixture model complexity with small sample sizes.

These cell-by-cell analyses revealed heterogeneity in adipose tissue myeloid progenitor cells with at least two VEGFR1-based subpopulations existing: 42.3% of the myeloid progenitor cells presented a high concentration of VEGFR1 on the cell membrane, 28,400 VEGFR1/cell; and the remaining myeloid progenitor cells (57.7%) had 8,020 VEGFR1/cell. Moreover, most adipose tissue myeloid progenitor cells overexpressed membrane VEGFR2, with 74,300 VEGFR2/cell, while 26% expressed 15,600 VEGFR2/cell. Lastly, 93.5% of adipose tissue myeloid progenitor cells expressed 1,670 VEGFR3/cell with a heavy tail averaging 8,660 VEGFR3/cell. It is the first time VEGFR concentrations have been reported on mouse myeloid progenitor cells. The high VEGFR2 expression on myeloid progenitor cells indicates that the myeloid progenitor cells are pro-angiogenic.

Figure 9:
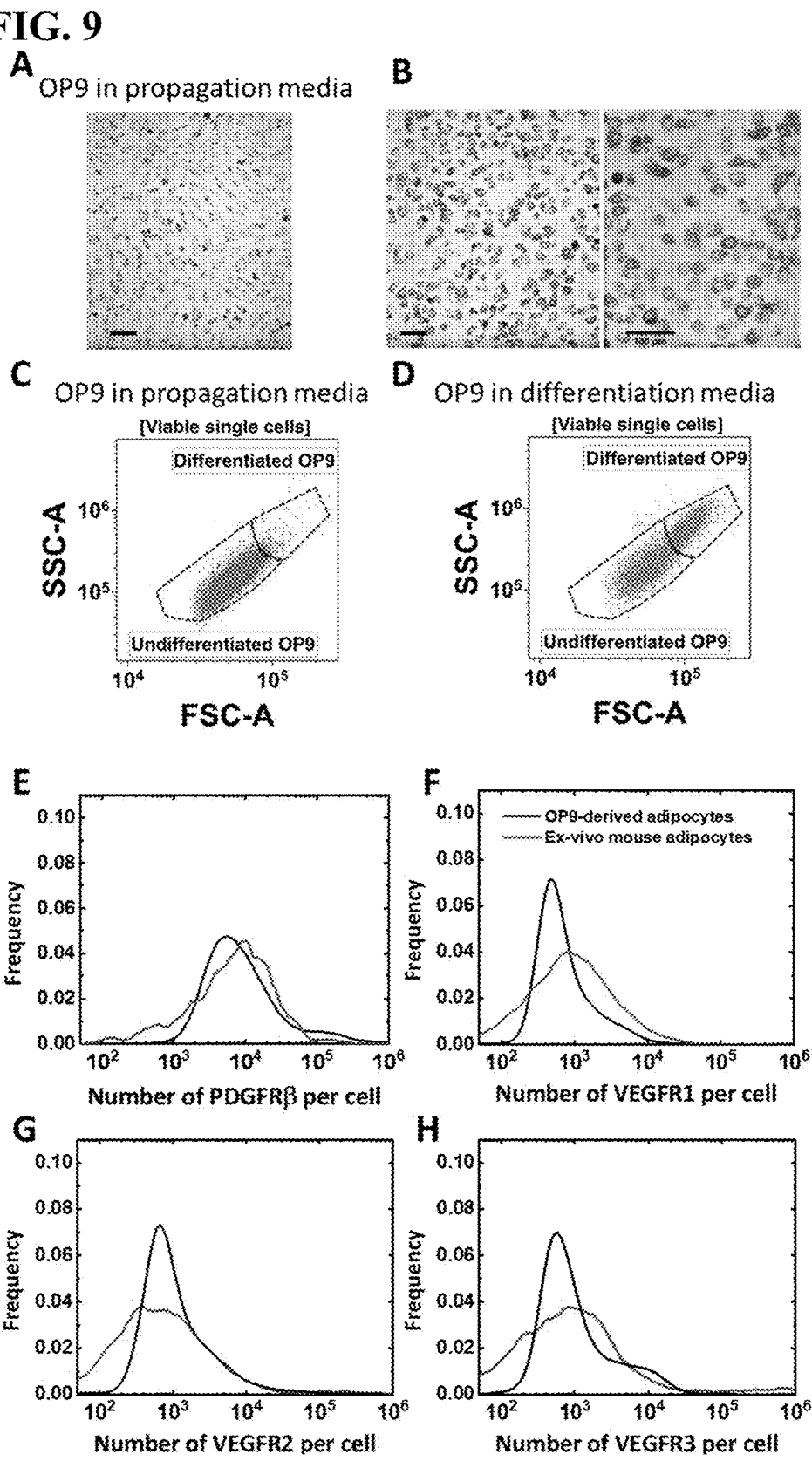
FIG. 9 panels E-H show cell-by cell distributions of VEGFRs and PDGFRβ on OP9-derived mouse adipocytes (black curves) and ex-vivo mouse adipocytes (grey curves).

Mouse adipocytes were differentiated from mouse stromal cell line OP9 via previously established protocol. OP9 cells retained stromal cell morphology in propagation media (FIG. 9, panel A), and gained adipocyte morphology and formed lipid droplets in differentiation media (FIG. 9, panel B). We separated the differentiated adipocytes from the undifferentiated OP9 cells based on cell size and internal granularity in flow cytometry (FIG. 9, panels C and D). Adipocytes are known to be derived from PDGFRβ+ pre-adipocytes (M. Shao, et al. nat. comm. 2018.)—we thus speculated that adipocytes express PDGFRβ. We compared PDGFRβ distributions in the OP9-derived adipocytes and ex-vivo mouse adipocytes, and found the distributions are closely overlapped and the median of each distribution is similar, 7,400 vs. 7,600 PDGFRβ per adipocyte, respectively (FIG. 9, panel E). This similarity of PDGFRβ distributions implies that the in-vitro OP9 adipocytes are promising substitutes of ex-vivo mouse adipocytes for basic biology research. We then profiled VEGFR1, VEGFR2, and VEGFR3 distributions in the OP9-derived adipocytes and compared them with the counterparts from mouse visceral adipose tissue (FIG. 9, panels F-H). We observed that the VEGFR concentrations are similarly low in both adipocyte populations.

Figure 10:
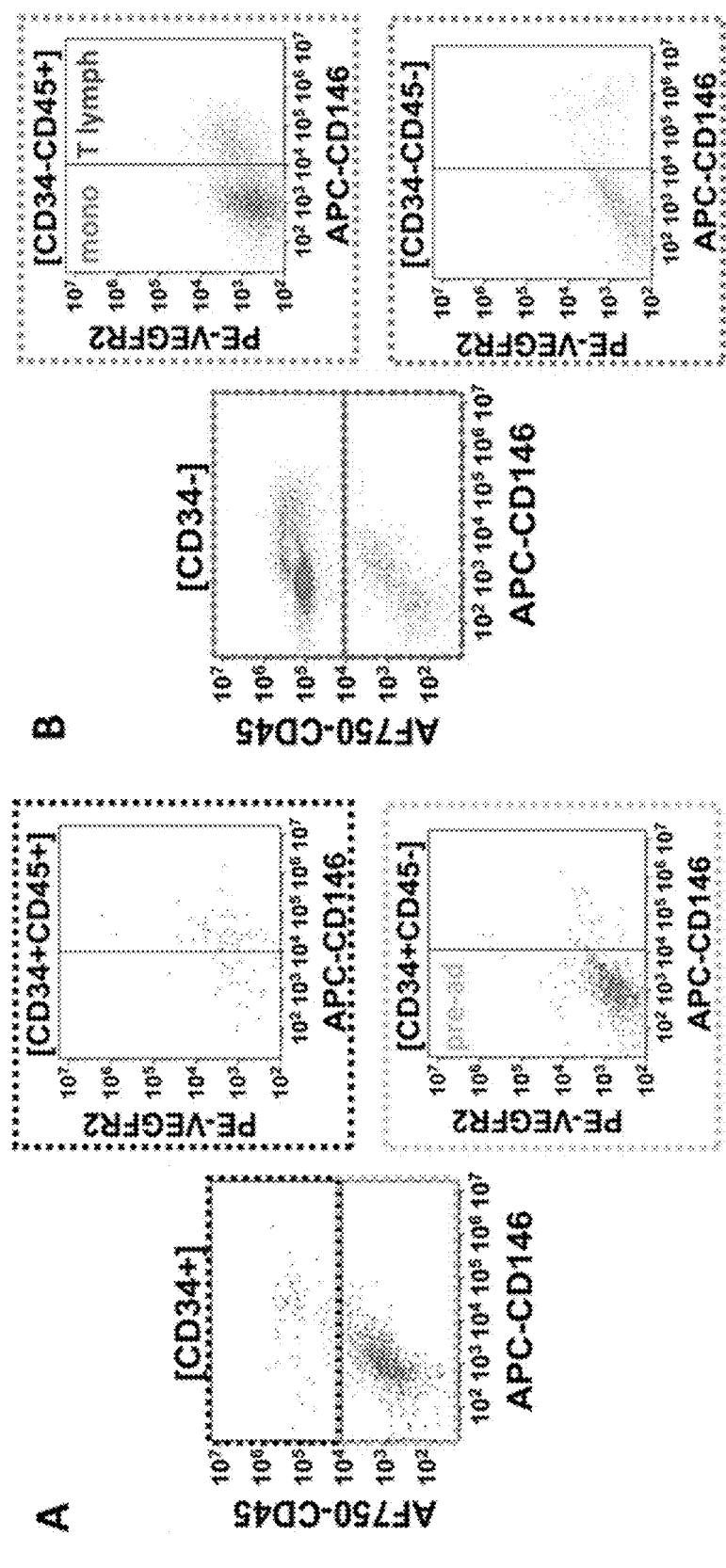
FIG. 10 shows cell composition in human lipedema patients' subcutaneous fat depots. Three major cell types are identified: pre-adipocytes (CD34+CD45–CD146–), monocyte-like cells (CD34–CD45+CD146–), and activated T lymphocytes (CD34–CD45+CD146+).
Figure 10:
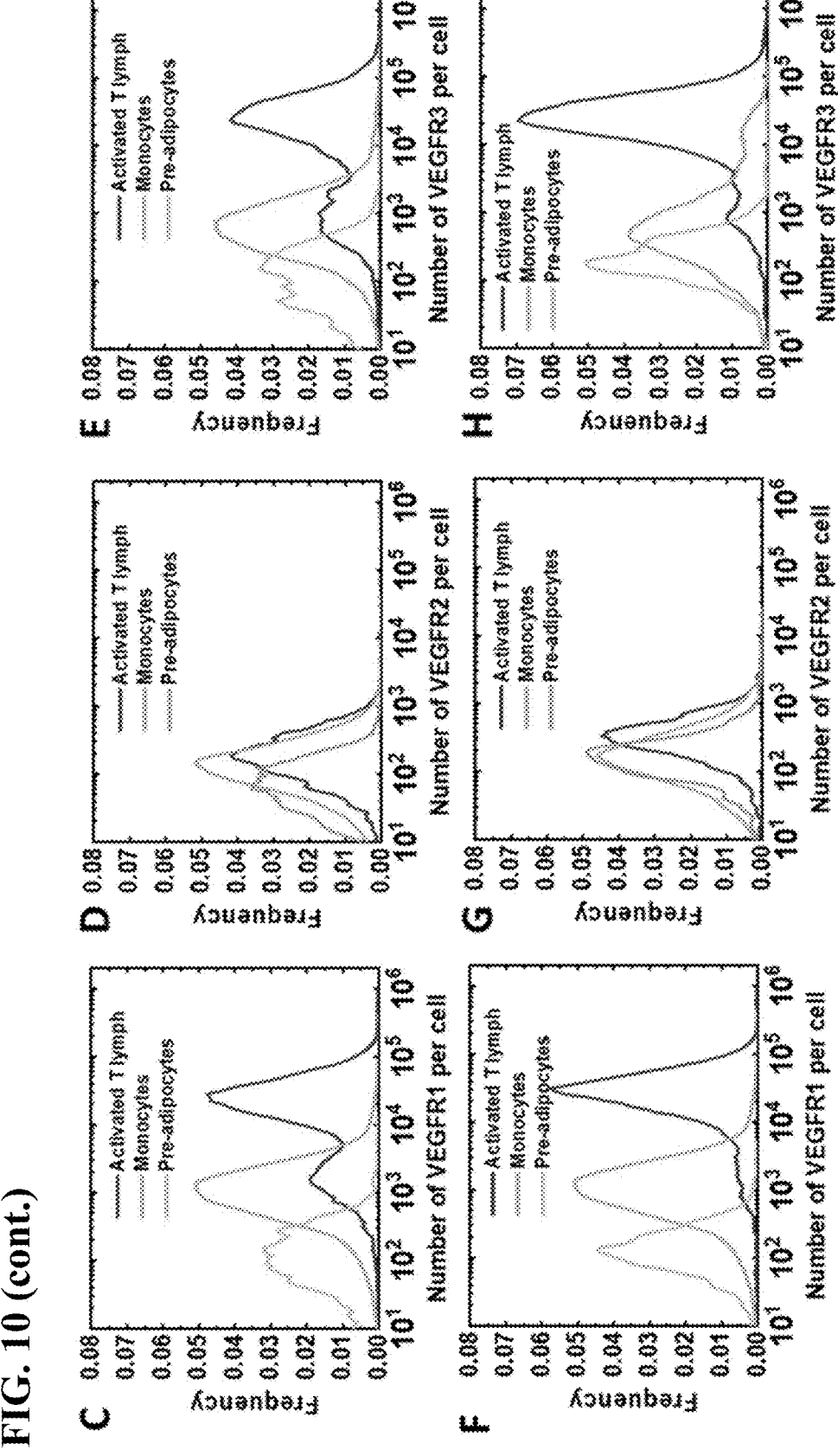

Example 3: a Pilot Study: Characterizing Upregulation of VEGF Receptors in Obese Adipose Tissues Via Single Cell Proteomic Analysis Materials and Methods: Women with lower-body obesity (lipedema) were recruited to the Center of Human Nutrition, Washington University. Subcutaneous adipose tissue biopsies were obtained from abdominal (upper-body) and femoral (lower-body) regions of each participant. Adipose SVFs were separated into four fractions via both CD34 immunomagnetic bead isolation and staining with APC-CD146 and APC-Cy7-CD45 and SYTOX™ blue (a viability indicator dye) and analyzed via multi-parametric flow cytometry. Based on previous mouse adipose tissue cell surface marker phenotyping, we identified three putative adipose tissue cell subtypes, including activated T lymphocytes (CD34⁻CD45⁺ CD146⁺), inactivated lymphocytes or monocytes (CD34⁻ CD45⁺CD146⁻), and stromal mixture (CD34⁻CD45⁻ CD146⁻) (FIG. 10). We quantified membrane VEGFRs using PE-conjugated VEGFR antibodies and Quantibrite™ PE beads and analyzed VEGFR concentrations ([VEGFR]) via single-cell analysis. Standard error of the mean (SEM) is used to denote error.

Results and Discussion: Both upper-body and lower-body (lipedema) obese samples exhibited bimodal [VEGFR1] on activated T lymphocytes. However, lower-body adipose SVF samples had more cells with high [VEGFR1]: 79.1% had 29,300 VEGFR1/cell while upper-body samples had 63.4% of these cells presenting 24,900 VEGFR1/cell (FIG. 10). The same trend was observed with [VEGFR3] lower-body obese adipose SVF samples, they had more cells with high [VEGFR3]: 77.4% had 25000 VEGFR3/cell while upper-body obese samples had 59.5% presenting 26,300 VEGFR3/cell (FIG. 10).

Conclusion: Our pilot study identified that lower-body lipedema SVFs have more activated T lymphocytes expressing high [VEGFR1] and high [VEGFR3] than upper-body less-obese SVFs. In these two lipedema patients, we did not see VEGFR2-overexpressing adipose tissue activated T lymphocytes as those seen in visceral fat from non-obese mice. The data indicates a need for larger subject analysis to determine if the differential targeting of VEGFRs could improve obesity therapies. These data can also be used to parametrize computational models to advance angiogenic therapies for treating obesity.

Example 4: VEGF and PDGF: Exploring Canonical and Non-Canonical Binding and Signaling Angiogenesis is a key pathogenic component of at least 70 known diseases, including: diabetes, Crohn's disease, and obesity. It is primarily driven by the vascular endothelial growth factor receptor (VEGFR) and its family of VEGF ligands. However, targeting VEGF alone has not achieved the promise of stable vascular control. We know that this is because angiogenesis involves several signaling axes, in addition to VEGF, representing a complexity that cannot be captured by targeting one growth factor alone. There is a need to shift our pedagogy: away from a uni-axis understanding of vascularization (e.g. VEGF-alone) towards a multi-axis understanding (e.g., VEGF+PDGF, etc.).

Towards this goal, we applied an experimental and computational, systems biology framework to examine a promising theory of receptor regulation: cross-family signaling, wherein ligands from one growth factor family bind to and signal through receptor(s) of another family. We measured the cross-family binding affinities of recombinant PDGFs: VEGFR2 via surface plasmon resonance. We constructed and simulated deterministic computational models of cross-family PDGF:VEGFR2 binding using MATLAB® SimBiology®. Finally, we measured PDGF-mediated phosphorylation of VEGFR2 tyrosines and VEGFR2 signaling adaptor-effectors on human umbilical vein endothelial cells (HUVECs) via enzyme-linked immunosorbent assays (ELISAs).

Our measurements revealed high-affinity binding between PDGFs and VEGFR2 (FIG. 12). Indeed, PDGFs-AB, —BB, and -CC have a higher binding affinity to VEGFR2 than they do to their canonical PDGFR binding partners. Our computational models identified several physiological conditions where PDGF:VEGFR2 binding interactions could dominate, including conditions of high VEGFR2 concentrations on the plasma membrane (FIG. 13) and when PDGF degradation is inhibited. Furthermore, we observed significant PDGF:VEGFR2 signaling. We observed phosphorylation of three VEGFR2 tyrosine residues; Y951, Y1054/59 and Y1175 (FIG. 14). We also observed significant PDGF-mediated phosphorylation of FAK, PI3K, PLCγ, and Src; adaptor-effectors of VEGFR2.

Our identification, measurement, and simulation of these novel cross-family interactions should catalyze a perspective shift in the areas of cell signaling, systems biology, and the clinical sciences. We show significant PDGF binding and signaling via VEGFR2, providing previously unknown knowledge of this new signaling paradigm. We demonstrate a new computational framework for exploring and manipulating cross-family signaling. Overall, this work provides focused insight into one combination of interactions (PDGF: VEGFR2), while expanding the role of growth factor signaling with significance to health and disease.

Example 5: Two Subtypes of Circulating Endothelial-Like Cells in the Blood and their Hypothetical Origins We obtained blood samples from 23 healthy subjects (11 females and 12 males). Subject characteristics such as age, sex, and race are listed in Supp. Table 1. The ages ranged between 25 to 60 years old (y/o), with a mean of 45.6 years (SD=11.1). The subjects were Black (non-Hispanic) (52.2%, n=12), White (non-Hispanic) (26.1%, n=6), and Hispanic (21.7%, n=5).

We used quantitative flow cytometry (qFlow) to acquire single-cell VEGFR measurements, and then we characterized the VEGFR distributions in CD34+CD31+ cPCs and CD34+CD31+CD146+ cECs using our established cell-by-cell analysis algorithms and mixture modeling.

We obtained fully quantitative values of the surface VEGFR concentrations from cPCs and cECs, and we were able to establish cell-by-cell VEGFR distributions for any individual's cPCs (FIG. 19, panels A and B) and cECs (FIG. 19, panels D and E). cECs exhibited greater VEGFR heterogeneity, ranging widely from 1,000 to 100,000 VEGFRs/cEC (FIG. 19, panels D and E). cPCs, in comparison, exhibited lower average VEGFR1 concentrations and little-to-no VEGFR2. Notably, these cECs generally possessed higher VEGFR concentrations than in-vitro endothelial cell cultures (FIG. 19, panel F), which have been reported to express 800 VEGFR1s/cell and 1,800 VEGFR2s/cell on average. The VEGFR distributions in cPCs (FIG. 19, panel C) and in cECs (FIG. 19, panel F) of individual subjects are described by the median and interquartile ranges (IQRs). The descriptive values provide baseline parameters for systems biology researchers to train computational models and test whether these circulating cells are useful surrogates for predicting VEGFR signaling in the original blood vessels.

Given that blood VEGF concentrations are significantly higher in postmenopausal females than in premenopausal females, and that postmenopausal females are at higher risk for many vascular diseases, we speculated that the heterogeneous VEGFR distributions in cPCs and cECs could be at least partially associated with menopausal status in females. Because all the females in this study above 50 y/o self-reported as postmenopausal, we used age 50 y/o as a cutoff for statistical interpretation of the effects of age on surface VEGFR concentrations on cECs and cPCs from the healthy males and females.

We discovered significant effects of age on the VEGFR concentrations of cPCs in females, but not those of males. We first assessed the relationship between VEGFR concentrations and the three independent factors of sex, race, and age. No factor was significantly associated with VEGFR concentrations on its own. Moreover, VEGFR concentrations were not significantly correlated with sex by race or with age by race. However, after adjusting for race, there was a significant sex by age correlation for six VEGFR outcomes (all in log scale) (Table 1). Specifically, VEGFR1 concentrations were significantly higher on cPCs in post-menopausal females (50-60 y/o) than premenopausal females (25-41 y/o, p=0.0035) and age-matched males (52-57 y/o, p=0.0251). On cECs, however, VEGFR1 concentrations were significantly higher in premenopausal females than postmenopausal females (p=0.01), age-matched males (28-44 y/o, p=0.0054), and older males (52-57 y/o, p=0.0048). Moreover, VEGFR2 concentrations on cECs were also significantly higher in premenopausal females than postmenopausal females (p=0.0187). Overall, the VEGFR concentrations of cPCs and cECs were significantly different between postmenopausal females and premenopausal females, but there was no significant effect of age in males.

In light of the significant differences we found in VEGFR concentrations between postmenopausal and premenopausal females, we separately pooled these two groups of blood samples to isolate the non-pathological effect on the VEGFR distribution patterns in cPCs and cECs.

Indeed, cPCs generally exhibited right-shifted VEGFR1 distributions in postmenopausal females relative to premenopausal females, as demonstrated by the cell-by-cell VEGFR1 distribution curves for all individual females (FIG. 20). By pooling the individual samples, we established reference ranges of VEGFR1 separately for postmenopausal females and premenopausal females (FIG. 20). The pooled VEGFR1 distributions show a median of 650 VEGFR1s/cPC for postmenopausal females, but only 88 VEGFR1s/cPC for premenopausal females. Similarly, the VEGFR1 distributions were separately pooled for males above and below 50 y/o to investigate age effects (Table 2). Notably, non-specific binding of human VEGFR antibodies to the cell membrane yielded 200-500 VEGFRs/cell on average 36. Thus, VEGFR1 expression by cPCs was considered negligible in three groups: premenopausal females (88 VEGFR1s/cPC), males above 50 (250 VEGFR1s/cPC), and males under 50 y/o (330 VEGFR1s/cPC). Similarly, VEGFR2 expression by cPCs in all healthy blood samples (<200 VEGFR2s/cPC) was considered negligible.

We then pooled VEGFR measurements of cECs and observed greater heterogeneity of VEGFR distributions in premenopausal females than in males and postmenopausal females. The distributions of VEGFR1 and VEGFR2 clustered around 3,000 VEGFRs/cell in the postmenopausal group, while they were heterogeneously widespread in the premenopausal group. By utilizing mixture modeling, we identified VEGFR-low, -intermediate, and -high cEC subpopulations and quantitatively characterized them by their different VEGFR concentrations. Briefly, cECs include VEGFR-intermediate and VEGFR-high subpopulations in the premenopausal females, (FIG. 21A, panels A and B), while such cEC subpopulations are not seen in the postmenopausal group (FIG. 21A, panels C and D). It is clear the VEGFR-intermediate and VEGFR-high cEC subpopulations in premenopausal females contribute to the overall VEGFR heterogeneity seen in females (FIG. 21B, panels E and F). We have shown that the VEGFR concentrations on cECs do not differ in males, using 50 y/o as a cutoff (Table 2): pooled cell-by-cell VEGFR data show that males' cECs include a VEGFR-intermediate/high subpopulation, and the size of this cEC subpopulation is smaller than that in premenopausal females (25% vs. 50%) (FIG. 21B, panels G and H).

Our data imply that the compositions of cEC subpopulations vary among postmenopausal females, premenopausal females, and males: (1) cECs in postmenopausal females were mainly VEGFR-low, presenting ~3,000 VEGFR1s and ~3000 VEGFR2s per cell, (2) half of the cEC population in the premenopausal female group presented intermediate-to-high VEGFRs on average, i.e. 138,000 VEGFR1s/cell and 39,000 to 236,000 VEGFR2s/cell, and (3) a quarter of the cEC population in males presented high VEGFRs, i.e., 206,000 VEGFR1s/cell and 155,000 VEGFR2s/cell on average (FIG. 22).

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions, methods, and processes without departing from the scope of the invention, it is intended that all matter contained in the above description shall be interpreted as illustrative and not in a limiting sense.

REFERENCES

1. Cao, Y. Angiogenesis and vascular functions in modulation of obesity, adipose metabolism, and insulin sensitivity. Cell Metab. 18, 478-489 (2013).

2. Lemoine, A. Y., Ledoux, S. & Larger, E. Adipose tissue angiogenesis in obesity. Thromb. Haemost. 110, 661-669 (2013).

3. Cao, Y. Angiogenesis as a therapeutic target for obesity and metabolic diseases. Chem. Immunol. Allergy 99, 170-179 (2014).

4. Silvia Corvera, O. G. Adipose Tissue Angiogenesis: Impact on Obesity and Type-2 Diabetes. Biochim Biophys Acta (2014). doi:10.1016/j.bbadis.2013.06.003.Adipose 5. Fukumura, D. et al. Paracrine Regulation of Angiogenesis and Adipocyte Differentiation During In Vivo Adipogenesis. Circ. Res. (2003). doi:10.1161/01.res.0000099243.20096.fa 6. Elias, I. et al. Adipose tissue overexpression of vascular endothelial growth factor protects against diet-induced obesity and insulin resistance. Diabetes 61, 1801-1813 (2012).

7. Weddell, J. C. & Imoukhuede, P. I. Quantitative characterization of cellular membrane-receptor heterogeneity through statistical and computational modeling. PLoS One 9, (2014).

8. Weddell, J. C. & Imoukhuede, P. I. Integrative meta-modeling identifies endocytic vesicles, late file:///C:/Users/cherifang/Dropbox/Professional References/Obesity/Flow cytometric single cell analysis reveals heterogeneity between adipose depots.pdfendosome and the nucleus as the cellular. Integr. Biol. (United Kingdom) 9, 464-484 (2017).

9. Chen, S., Le, T., Harley, B. A. C. & Imoukhuede, P. I. Characterizing Glioblastoma Heterogeneity via Single-Cell Receptor Quantification. Front. Bioeng. Biotechnol. 6, 92 (2018).

10. Imoukhuede, P. I. & Popel, A. S. Quantitative fluorescent profiling of VEGFRs reveals tumor cell and endothelial cell heterogeneity in breast cancer xenografts. Cancer Med. 3, 225-244 (2014).

11. Imoukhuede, P. I., Dokun, A. O., Annex, B. H. & Popel, A. S. Endothelial cell-by-cell profiling reveals the temporal dynamics of VEGFR1 and VEGFR2 membrane localization after murine hindlimb ischemia. AJP Hear. Circ. Physiol. 304, H1085-H1093 (2013).

12. Imoukhuede, P. I. & Popel, A. S. Expression of VEGF Receptors on Endothelial Cells in Mouse Skeletal Muscle. PLoS One 7, (2012).

13. Imoukhuede, P. I., Dokun, A. O., Annex, B. H. & Popel, A. S. Endothelial cell-by-cell profiling reveals the temporal dynamics of VEGFR1 and VEGFR2 membrane localization after murine hindlimb ischemia. Am. J. Physiol. Heart Circ. Physiol. 304, H1085-93 (2013).

14. Chen, S., Guo, X., Imarenezor, O. & Imoukhuede, P. I. Quantification of VEGFRs, NRP1, and PDGFRs on Endothelial Cells and Fibroblasts Reveals Serum, Intra-Family Ligand, and Cross-Family Ligand Regulation. Cell. Mol. Bioeng. 8, 383-403 (2015).

15. Angiogenesis, C., Reveals, M. & Chen, S. Endothelial Heterogeneity. 1-21 (2019).

16. Weddell, J. C., Chen, S. & Imoukhuede, P. I. VEGFR1 promotes cell migration and proliferation through PLCγ and PI3K pathways. npj Syst. Biol. Appl. (2018). doi:10.1038/s41540-017-0037-9

17. Weddell, J. C. & Imoukhuede, P. I. Computational Systems Biology for the VEGF Family in Angiogenesis. Encyclopedia of Cardiovascular Research and Medicine (Elsevier Inc., 2018). doi:10.1016/B978-0-12-809657-4.99548-6

18. Mamer, S. B. et al. Discovery of High-Affinity PDGF-VEGFR Interactions: Redefining RTK Dynamics. Sci. Rep. 7, 1-14 (2017).

19. Grimstein, M. et al. Physiologically Based Pharmacokinetic Modeling in Regulatory Science: An Update From the U.S. Food and Drug Administration's Office of Clinical Pharmacology. Journal of Pharmaceutical Sciences (2019). doi:10.1016/j.xphs.2018.10.033

20. Bordbar, A., Monk, J. M., King, Z. A. & Palsson, B. O. Constraint-based models predict metabolic and associated cellular functions. Nature Reviews Genetics 15, 107-120 (2014).

21. Meng, Q., Makinen, V. P., Luk, H. & Yang, X. Systems Biology Approaches and Applications in Obesity, Diabetes, and Cardiovascular Diseases. Current Cardiovascular Risk Reports 7, 73-83 (2013).

22. Drake, T. A. Genes and pathways contributing to obesity: a systems biology view. Prog. Mol. Biol. Transl. Sci. 94, 9-38 (2010).

23. Winterbach, W., Mieghem, P. Van, Reinders, M., Wang, H. & Ridder, D. de. Topology of molecular interaction networks. BMC Syst. Biol. 7, 90 (2013).

24. Pavlopoulos, G. A. et al. Using graph theory to analyze biological networks. BioData Min. 4, 10 (2011).

25. Stelling, J. Mathematical models in microbial systems biology. Current Opinion in Microbiology 7, 513-518 (2004).

26. Lewis, N. E., Nagarajan, H. & Palsson, B. O. Constraining the metabolic genotype-phenotype relationship using a phylogeny of in silico methods. Nature Reviews Microbiology 10, 291-305 (2012).

27. Smit, C., De Hoogd, S., Bruggemann, R. J. M. & Knibbe, C. A. J. Obesity and drug pharmacology: a review of the influence of obesity on pharmacokinetic and pharmacodynamic parameters. Expert Opinion on Drug Metabolism and Toxicology (2018). doi:10.1080/17425255.2018.1440287

28. Hanley, M. J., Abernethy, D. R. & Greenblatt, D. J. Effect of obesity on the pharmacokinetics of drugs in humans. Clin. Pharmacokinet. 49, 71-87 (2010).

29. Emond, C., DeVito, M. J., Diliberto, J. J. & Birnbaum, L. S. The Influence of Obesity on the Pharmacokinetics of Dioxin in Mice: An Assessment Using Classical and PBPK Modeling. Toxicol. Sci. 164, 218-228 (2018).

30. Jo, J. et al. Hypertrophy and/or hyperplasia: Dynamics of adipose tissue growth. PLoS Comput. Biol. 5, (2009).

31. Finley, S. D., Dhar, M. & Popel, A. S. Compartment Model Predicts VEGF Secretion and Investigates the Effects of VEGF Trap in Tumor-Bearing Mice. Front. Oncol. (2013). doi:10.3389/fonc.2013.00196

32. Chu, L. H. et al. A multiscale computational model predicts distribution of anti-angiogenic isoform VEGF165b in peripheral arterial disease in human and mouse. Sci. Rep. (2016). doi:10.1038/srep37030

33. Erban, R., Chapman, S. J. & Maini, P. K. A PRACTICAL GUIDE TO STOCHASTIC SIMULATIONS OF REACTION-DIFFUSION PROCESSES.

34. Masuda, N. & Rocha, L. E. C. A Gillespie algorithm for non-Markovian stochastic processes: Laplace transform approach. arxiv:1601.01490 (2016).

35. Dada, J. O. & Mendes, P. Multi-scale modelling and simulation in systems biology. Integrative Biology 3, 86-96 (2011).

36. Walpole, J. et al. Agent-based model of angiogenesis simulates capillary sprout initiation in multicellular networks. Integr. Biol. (United Kingdom) (2015). doi: 10.1039/c5ib00024f 37. Bentley, K., Gerhardt, H. & Bates, P. A. Agent-based simulation of notch-mediated tip cell selection in angiogenic sprout initialisation. J. Theor. Biol. 250, 25-36 (2008).

38. Wu, F. T. H. et al. A systems biology perspective on sVEGFR1: its biological function, pathogenic role and therapeutic use. J. Cell. Mol. Med. 14, 528-52 (2010).

39. Meier-Schellersheim, M., Fraser, I. D. C. & Klauschen, F. Multiscale modeling for biologists. Wiley Interdiscip. Rev. Syst. Biol. Med. 1, 4-14 (2009).

40. Castiglione, F., Pappalardo, F., Bianca, C., Russo, G. & Motta, S. Modeling biology spanning different scales: An open challenge. BioMed Research International 2014, (2014).

41. Walpole, J., Papin, J. A. & Peirce, S. M. Multiscale Computational Models of Complex Biological Systems. Annu. Rev. Biomed. Eng. 15, 137-154 (2013).

42. Qu, Z., Garfinkel, A., Weiss, J. N. & Nivala, M. Multi-scale modeling in biology: How to bridge the gaps between scales?Progress in Biophysics and Molecular Biology 107, 21-31(2011).

43. Gallagher Advisor, S. & Eddy, W. F. Comparing compartment and agent-based models. (2017).

44. Figueredo, G. P., Siebers, P.-O., Owen, M. R., Reps, J. & Aickelin, U. Comparing Stochastic Differential Equations and Agent-Based Modelling and Simulation for Early-Stage Cancer. PLoS One 9, e95150 (2014).

45. Simons, M. An inside view: VEGF receptor trafficking and signaling. Physiology (2012). doi:10.1152/physiol.00016.2012

46. Simons, M., Gordon, E. & Claesson-Welsh, L. Mechanisms and regulation of endothelial VEGF receptor signalling. Nat. Rev. Mol. Cell Biol. 17, 611-625 (2016).

47. Waltenberger, J., Claesson-Welsh, L., Siegbahn, A., Shibuya, M. & Heldin, C. H. Different signal transduction properties of KDR and Fltl, two receptors for vascular endothelial growth factor. J. Biol. Chem. 269, 26988-26995 (1994).

48. Cao, Y. Positive and negative modulation of angiogenesis by VEGFR1 ligands. Sci. Signal. 2, 1-12 (2009).

49. Sina, K., Sonia, T., Xiujuan, L., Laura, G. & Lena, C. Signal transduction by vascular endothelial growth factor receptors. Biochem. J. 1-21 (2011).

50. Lafontan, M. et al. Adipose Tissue Endothelial Cells From Obese Human Subjects: Differences Among Depots in Angiogenic, Metabolic, and Inflammatory Gene Expression and Cellular Senescence. Diabetes 59, 2755-2763 (2010).

51. Voros, G. et al. Modulation of angiogenesis during adipose tissue development in murine models of obesity. Endocrinology 146, 4545-4554 (2005).

52. Imoukhuede, P. I. & Popel, A. S. Quantification and cell-to-cell variation of vascular endothelial growth factor receptors. Exp. Cell Res. 317, 955-965 (2011).

53. Weickhardt, A. J. et al. Vascular endothelial growth factor D expression is a potential biomarker of bevacizumab benefit in colorectal cancer. Br. J. Cancer 113, 37-45 (2015).

54. Weddell, J. C. & Imoukhuede, P. I. Integrative meta-modeling identifies endocytic vesicles, late endosome and the nucleus as the cellular compartments primarily directing RTK signaling. Integr. Biol. (United Kingdom) 9, 464-484 (2017).

55. Dalton, H. J. et al. Macrophages facilitate resistance to anti-VEGF therapy by altered VEGFR expression. Clin. Cancer Res. 23, 7034-7046 (2017).

56. Chen, S. et al. qFlow cytometry-based receptoromic screening: a high-throughput quantification approach informing biomarker selection and nanosensor development. in Methods Mol Biol (eds. Hurst Petrosko, S. & S. Day, E.) 117-138 (Springer New York, 2017).

57. Breitling, R. What is systems biology?Front. Physiol. 1 MAY, 1-5 (2010).

58. Gao, J. et al. Characterization of OP9 as authentic mesenchymal stem cell line. J. Genet. Genomics 37, 475-482 (2010).

59. Wolins, N. E. et al. OP9 mouse stromal cells rapidly differentiate into adipocytes: characterization of a useful new model of adipogenesis. J. Lipid Res. 47, 450-460 (2006).

60. Baker, N. A., Muir, L. A., Lumeng, C. N. & O'Rourke, R. W. Differentiation and Metabolic Interrogation of Human Adipocytes. Methods Mol. Biol. 1566, 61-76 (2017).

61. Boumelhem, B. B., Assinder, S. J., Bell-Anderson, K. S. & Fraser, S. T. Flow cytometric single cell analysis reveals heterogeneity between adipose depots. Adipocyte 6, 112-123 (2017).

62. Klar, A. S. et al. Characterization of vasculogenic potential of human adipose-derived endothelial cells in a three-dimensional vascularized skin substitute. Pediatr. Surg. Int. 32, 17-27 (2016).

63. Chopra, H., Hung, M. K., Kwong, D. L., Zhang, C. F. & Pow, E. H. N. Insights into endothelial progenitor cells: Origin, classification, potentials, and prospects. Stem Cells Int. 2018, (2018).

64. Luo, Y. et al. Macrophagic CD146 promotes foam cell formation and retention during atherosclerosis. Cell Res. 27, 352-372 (2017).

65. Baer, P. C. Adipose-derived mesenchymal stromal/stem cells: An update on their phenotype in vivo and in vitro. World J. Stem Cells 6, 256 (2014).

66. Silva, K. R. et al. Stromal-vascular fraction content and adipose stem cell behavior are altered in morbid obese and post bariatric surgery ex-obese women. Stem Cell Res. Ther. 6, 1-13 (2015).

67. Goldman, O. et al. KDR identifies a conserved human and murine hepatic progenitor and instructs early liver development. Cell Stem Cell (2013). doi:10.1016/j.stem.2013.04.026

68. Incio, J. et al. PlGF/VEGFR-1 signaling promotes macrophage polarization and accelerated tumor progression in obesity. Clin. Cancer Res. 22, 2993-3004 (2016).

69. Murakami, M. et al. VEGFR1 tyrosine kinase signaling promotes lymphangiogenesis as well as angiogenesis indirectly via macrophage recruitment. Arterioscler. Thromb. Vasc. Biol. 28, 658-664 (2008).

70. Karaman, S. et al. Transgenic overexpression of VEGF-C induces weight gain and insulin resistance in mice. Sci. Rep. 6, 1-12 (2016).

71. Arterbery, A. S. & Bogue, C. W. Hhex is necessary for the hepatic differentiation of mouse ES cells and acts via Vegf signaling. PLoS One 11, 1-19 (2016).

72. J. A. Mund, M. L. Estes, M. C. Yoder, D. A. Ingram, and J. Case, "Flow cytometric identification and functional characterization of immature and mature circulating endothelial cells," Arterioscler. Thromb. Vasc. Biol., vol. 32, no. 4, pp. 1045-1053, 2012.

73. M. L. Estes, J. A. Mund, D. A. Ingram, and J. Case, "Identification of endothelial cells and progenitor cell subsets in human peripheral blood," Curr. Protoc. Cytom., no. SUPPL. 52, 2010.

74. I. Martin-Padura and F. Bertolini, "Circulating endothelial cells as biomarkers for angiogenesis in tumor progression," Front Biosci (Schol Ed), vol. 1, no. 3, pp. 304-318, 2009.

75. L. Pietrzyk, "Biomarkers Discovery for Colorectal Cancer: A Review on Tumor Endothelial Markers as Perspective Candidates," Dis. Markers, vol. 2016, 2016.

76. S. M. Watt, A. Athanassopoulos, A. L. Harris, and G. Tsaknakis, "Human endothelial stem/progenitor cells, angiogenic factors and vascular repair," J. R. Soc. Interface, vol. 7, no. SUPPL. 6, 2010.

77. L. Eidenschink, G. Dizerega, K. Rodgers, M. Bartlett, D. A. Wells, and M. R. Loken, "Basal levels of CD34 positive cells in peripheral blood differ between individuals and are stable for 18 months," Cytom. Part B—Clin. Cytom., vol. 82 B, no. 1, pp. 18-25, 2012.

78. M. Steurer et al., "Quantification of circulating endothelial and progenitor cells: comparison of quantitative PCR and four-channel flow cytometry.," BMC Res. Notes, vol. 1, no. August 2017, p. 71, 2008.

79. B. Delorme et al., "Presence of endothelial progenitor cells, distinct from mature endothelial cells, within human CD146+ blood cells.," Thromb. Haemost., vol. 94, no. 6, pp. 1270-1279, December 2005.

80. M. Danova, G. Comolli, M. Manzoni, M. Torchio, and G. Mazzini, "Flow cytometric analysis of circulating endothelial cells and endothelial progenitors for clinical purposes in oncology: A critical evaluation.," Mol. Clin. Oncol., vol. 4, no. 6, pp. 909-917, 2016.

81. M. Marçola and C. E. Rodrigues, "Endothelial Progenitor Cells in Tumor Angiogenesis: Another Brick in the Wall," vol. 2015, 2015.

82. F. Bertolini, Y. Shaked, P. Mancuso, and R. Kerbel, "The multifaceted circulating endothelial cell in cancer: towards marker and target identification," Nat. Rev Cancer, vol. 6, no. 1474-175X (Print), pp. 835-845, 2006.

83. L. E. Sidney, M. J. Branch, S. E. Dunphy, H. S. Dua, and A. Hopkinson, "Concise review: Evidence for CD34 as a common marker for diverse progenitors," Stem Cells, vol. 32, no. 6, pp. 1380-1389, 2014.

84. K. Huizer, D. A. M. Mustafa, J. C. Spelt, J. M. Kros, and A. Sacchetti, "Improving the characterization of endothelial progenitor cell subsets by an optimized FACS protocol," PLoS One, vol. 12, no. 9, pp. 1-18, 2017.

85. P. I. Imoukhuede, A. O. Dokun, B. H. Annex, and A. S. Popel, "Endothelial cell-by-cell profiling reveals the temporal dynamics of VEGFR1 and VEGFR2 membrane localization after murine hindlimb ischemia.," Am. J. Physiol. Heart Circ. Physiol., vol. 304, no. 8, pp. H1085-93, 2013.

86. P. I. Imoukhuede and A. S. Popel, "Expression of VEGF Receptors on Endothelial Cells in Mouse Skeletal Muscle," PLoS One, vol. 7, no. 9, 2012.

87. S. Chen, J. C. Weddell, P. Gupta, G. Conard, J. Parkin, and P. I. Imoukhuede, "qFlow cytometry-based receptoromic screening: a high-throughput quantification approach informing biomarker selection and nanosensor development," in Methods Mol Biol, 2nd ed., S. Hurst Petrosko and E. S. Day, Eds. New York, NY: Springer New York, 2017, pp. 117-138.

88. S. Chen, X. Guo, O. Imarenezor, and P. I. Imoukhuede, "Quantification of VEGFRs, NRP1, and PDGFRs on Endothelial Cells and Fibroblasts Reveals Serum, Intra-Family Ligand, and Cross-Family Ligand Regulation," Cell. Mol. Bioeng., vol. 8, no. 3, pp. 383-403, 2015.

89. P. I. Imoukhuede and A. S. Popel, "Quantitative fluorescent profiling of VEGFRs reveals tumor cell and endothelial cell heterogeneity in breast cancer xeno-grafts," Cancer Med., vol. 3, no. 2, pp. 225-244, 2014.
90. J. C. Weddell and P. I. Imoukhuede, "Quantitative characterization of cellular membrane-receptor heterogeneity through statistical and computational modeling," PLoS One, vol. 9, no. 5, 2014.

The invention claimed is:

1. A method of determining the suitability of an anti-angiogenesis treatment in an obese subject and administering the anti-angiogenesis treatment comprising:

(a) isolating stromal vascular fraction (SVF) from an adipocyte tissue sample obtained from the subject;

(b) isolating a subpopulation of cells from the SVF using flow cytometry;

(c) quantifying levels of vascular endothelial growth factor (VEGF) receptors on cells;

(d) identifying the subject as a candidate for anti-angiogenesis treatment if the levels of VEGF on the isolated subpopulation of cells exceed a threshold of 24,900 VEGFR1/cell or 25,000 VEGFR3/cell; and (e) treating the subject identified as a candidate with anti-VEGF drug bevacizumab.

2. The method of claim 1, wherein the adipocyte tissue sample is derived from visceral or subcutaneous adipose tissue.

3. The method of claim 1, wherein the subpopulation of cells is selected from the group consisting of adipose tissue macrophages, endothelial cells, blood cells, endothelial progenitor cells, and preadipocytes.

4. The method of claim 1, wherein step (b) further comprises:

(i) labeling cells in the SVF with cell markers against CD31, CD45, and CD146;

(ii) isolating $CD31^+CD146^+CD45^+$ cells as adipose tissue macrophages; $CD31^+CD146^+CD45^-$ cells as endothelial cells, $CD31^+CD146^-CD45^+$ as blood cells, $CD31^+CD146^-CD45^-$ as endothelial progenitor cells, $CD31^-CD146^-CD45^-$ as preadipocytes and $CD31^-CD146^-CD45^+$ as unclassified cells.

5. The method of claim 1, wherein the step of quantifying VEGF receptors on cells comprises quantitative flow cytometry.

6. The method of claim 5, wherein the quantitative flow cytometry further comprises:

a) a cell-by-cell analysis of the stromal vascular fraction measuring a plurality of VEGF receptors for individual cells, thereby obtaining a VEGF receptor profile for one or more subpopulation of cells from the stromal vascular fraction, wherein said VEGF receptor profile parameters include concentrations of a plurality of plasma membrane VEGF receptors and, optionally, concentrations of one or more free plasma membrane VEGF receptor ligands;

b) determining a cell heterogeneity parameter characterizing the subpopulation of cells by applying a Bayesian Information Criterion model to analyze the VEGF receptor profile;

c) comparing the cell heterogeneity parameter to one or more cell heterogeneity reference values, thereby obtaining a classification of the cells.

7. The method of claim 1, further comprising applying a Bayesian Information Criterion model to analyze a Gaussian mixture model comprising 1-9 log-normal Gaussian sub-distributions.

8. The method of claim 7, wherein the Bayesian Information Criterion model is used to select the Gaussian mixture model with the lowest Bayesian Information Criterion.

9. The method of claim 1, wherein cell-by-cell analysis of the SVF cell population is carried out using one or more techniques selected from the group consisting of flow cytometry, surface plasma resonance and computational modeling.

10. The method of claim 1, wherein quantifying VEGF receptors comprises using phycoerythrin (PE)-conjugated calibration beads, wherein a mean PE fluorescence intensity value is translated to the absolute quantity of PE molecules per cell, wherein the number of PE molecules per cell is proportional to the number of VEGF receptors per cell.

* * * * *